(12) United States Patent
Beemer

(10) Patent No.: US 9,201,049 B2
(45) Date of Patent: Dec. 1, 2015

(54) CONNECTOR WITH STRUCTURAL REINFORCEMENT AND BIOCOMPATIBLE FLUID PASSAGEWAY

(71) Applicant: IDEX Health & Science LLC, Oak Harbor, WA (US)

(72) Inventor: Eric Beemer, Anacortes, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 501 days.

(21) Appl. No.: 13/799,454

(22) Filed: Mar. 13, 2013

(65) Prior Publication Data

US 2014/0260564 A1    Sep. 18, 2014

(51) Int. Cl.

| | |
|---|---|
| *F16L 33/24* | (2006.01) |
| *G01N 30/26* | (2006.01) |
| *F16L 31/00* | (2006.01) |
| *F16L 41/02* | (2006.01) |
| *G01N 30/60* | (2006.01) |
| *B01L 3/00* | (2006.01) |
| *B29C 45/14* | (2006.01) |

(52) U.S. Cl.
CPC ............ *G01N 30/26* (2013.01); *B01L 3/563* (2013.01); *B29C 45/14598* (2013.01); *F16L 31/00* (2013.01); *F16L 41/021* (2013.01); *G01N 30/6026* (2013.01); *G01N 30/6043* (2013.01); *B01L 2200/0689* (2013.01); *B01L 2300/0838* (2013.01); *B01L 2300/163* (2013.01); *B29C 45/14344* (2013.01); *F16L 33/24* (2013.01)

(58) Field of Classification Search
CPC ............ B01D 15/10; B01L 2200/0689; B01L 2300/163; F16L 33/24
See application file for complete search history.

(56) References Cited

U.S. PATENT DOCUMENTS

| | | | | |
|---|---|---|---|---|
| 3,771,659 | A | * 11/1973 | Fraser | G01N 30/603 210/198.2 |
| 4,280,905 | A | * 7/1981 | Gunkel | B01D 15/22 210/198.2 |
| 4,313,828 | A | * 2/1982 | Brownlee | B01D 15/08 210/198.2 |
| 4,522,715 | A | * 6/1985 | Walters | B01D 15/22 210/198.2 |
| 4,669,756 | A | * 6/1987 | Cassaday | F16L 47/00 285/24 |
| 5,472,598 | A | 12/1995 | Schick | |
| 5,525,303 | A | 6/1996 | Ford et al. | |
| 5,730,943 | A | 3/1998 | Ford et al. | |

(Continued)

OTHER PUBLICATIONS

Written Opinion for PCT/US2014/026713 mailed on Oct. 28, 2014.*

(Continued)

*Primary Examiner* — David A Rogers
(74) *Attorney, Agent, or Firm* — Vinson & Elkins LLP

(57) ABSTRACT

A connector with a biocompatible fluid passageway and method for manufacturing thereof is described. The biocompatible connector may be used in an analytical instrument (AI) system as a union, an adapter, a tee, a cross, a manifold, a valve, or for other fittings or components. The connector has a reinforcement insert and a biocompatible molding covering portions of the reinforcement insert. The reinforcement insert has a first portion, a second portion, and a middle portion between the first portion and the second portion. The first and second portions have threaded sections and each have a plurality of non-threaded sections. For a given portion, the junction of the non-threaded sections forms a lip by which to prevent the molded material from flowing into the threaded sections. In certain embodiments, an interior web is used in the reinforcement insert to provide additional structural support.

40 Claims, 38 Drawing Sheets

(56) References Cited

U.S. PATENT DOCUMENTS

| | | | |
|---|---|---|---|
| 5,736,036 A * | 4/1998 | Upchurch | B01D 15/22 210/198.2 |
| 6,070,912 A | 6/2000 | Latham | |
| 6,095,572 A | 8/2000 | Ford et al. | |
| 7,101,477 B1 * | 9/2006 | Willis | B01D 15/20 210/198.2 |
| 7,144,502 B2 | 12/2006 | Fermier et al. | |
| 7,311,502 B2 | 12/2007 | Gerhardt et al. | |
| 7,758,014 B2 * | 7/2010 | Lancaster | F16K 1/04 251/122 |
| 8,173,078 B2 | 5/2012 | Yao et al. | |
| 8,936,723 B2 * | 1/2015 | Nickerson | G01N 30/6026 210/198.2 |
| 2002/0176804 A1 | 11/2002 | Strand et al. | |
| 2009/0167016 A1 * | 7/2009 | Zapata | F16L 58/182 285/55 |
| 2009/0273182 A1 | 11/2009 | Lewis et al. | |
| 2010/0224543 A1 * | 9/2010 | Ellis | B01D 15/125 210/198.2 |
| 2010/0224546 A1 | 9/2010 | Ellis et al. | |
| 2011/0012280 A1 | 1/2011 | Deslauners et al. | |
| 2011/0049030 A1 * | 3/2011 | Nickerson | B01D 15/22 210/198.2 |
| 2011/0144766 A1 | 6/2011 | Kale et al. | |
| 2012/0024411 A1 | 2/2012 | Hahn et al. | |
| 2012/0160754 A1 | 6/2012 | Falk-Jordan | |
| 2012/0223520 A1 | 9/2012 | Graham | |
| 2012/0223522 A1 | 9/2012 | Graham | |

OTHER PUBLICATIONS

International Search Report for PCT/US2014/026713 mailed on Oct. 28, 2014.*

* cited by examiner

CONNECTOR WITH STRUCTURAL REINFORCEMENT AND BIOCOMPATIBLE FLUID PASSAGEWAY

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to an improved biocompatible connector and methods of making same for use in liquid chromatography and other analytical systems, and relates more particularly to a connector with a structural reinforcement and a biocompatible fluid passageway useful in a wide variety of fittings or assemblies, including but not limited to unions, adapters, tees, crosses, manifolds, valves, etc.

2. Description of the Related Art

Liquid chromatography (LC), ion chromatography (IC) and gas chromatography (GC) are well-known techniques used in analytical systems for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase. LC and related technologies, and associated tubing, ports, fittings, and other components are discussed in U.S. patent application Ser. No. 13/206,873 (published as US 2012/0024411), Ser. No. 13/292,667 (published as US 2012/0223520), and Ser. No. 13/686,260 (entitled "microfluidic interconnect"), each of which is incorporated herein by reference.

In a conventional LC system, the sample and mobile phase pass through one or more filters and often a guard column before coming to the column. A typical column usually consists of a piece of tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector, which can be built using MEMS technology. The detector detects the presence of specific molecules or compounds. Two general types of detectors are typically used in LC applications. One type measures a change in some overall physical property of the mobile phase and the sample (such as their refractive index). The other type measures some properties of only the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample. Additionally, LC systems may utilize mass spectrometric detection for identification and quantification of the sample, either in addition to, or as an alternative to, the conventional detectors described previously. Ion chromatography relies on the detection of ions in solution, so most metallic materials in the flow path can create interference in the detection scheme, as they create background ions.

In addition to the above components, an LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, and then connect a supply of the selected mobile phase and a selected column to the LC system before operation. In order to be suitable for high performance liquid chromatography (HPLC) applications, each connection must be able to withstand the typical operating pressures of the LC system. If the connection is too weak, it may leak. Because the types of solvents that are sometimes used as the mobile phase are often toxic and because it is often expensive to obtain and/or prepare many samples for use, any such connection failure is a serious concern. A high pressure fitting is further discussed in U.S. patent application Ser. No. 13/038,110 (published as U.S. Patent Publication No. US 2012/0223522 A1), the contents of which are incorporated herein by reference.

Most conventional HPLC systems include pumps which can generate relatively high pressures of up to around 5,000 psi to 6,000 psi or so. In many situations, an operator can obtain successful results by operating an LC system at "low" pressures of anywhere from just a few psi or so up to 1,000 psi or so. More often than not, however, an operator will find it desirable to operate a LC system at relatively "higher" pressures of over 1,000 psi. If a connection does not have sufficient structural strength, it could leak at higher pressures.

Another, relatively newer liquid chromatography form is Ultra High Performance Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Pat. No. 8,173,078 (entitled "Sample Injector System for Liquid Chromatography"), an injection system is described for use with UHPLC applications, which are said to involve pressures in the range from 20,000 psi to 120,000 psi. In U.S. Pat. No. 7,311,502 (entitled "Method for Using a Hydraulic Amplifier Pump in Ultrahigh Pressure Liquid Chromatography"), the use of a hydraulic amplifier is described for use in UHPLC systems involving pressures in excess of 25,000 psi. In U.S. Pat. No. 7,144,502 (entitled "Chromatography System with Gradient Storage and Method for Operating the Same"), a system for performing UHPLC is disclosed, with UHPLC described as involving pressures above 5,000 psi (and up to 60,000 psi). Applicants hereby incorporate by reference as if fully set forth herein U.S. Pat. Nos. 7,311,502; 7,14,502; and 8,173,078.

Given the desirability of need for leak-free connections, conventional connections have been made with stainless steel tubing and stainless steel end fittings. More recently, however, it has been realized that the use of stainless steel components in a LC system can have potential drawbacks in situations involving biological samples, and cannot be routinely used for ion chromatography. For example, the components in a sample may attach themselves to the wall of stainless steel tubing. This can present problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for biocompatible connections through the use of a material that is chemically inert with respect to such biological samples and the mobile phase used with such samples, so that ions will not be released by the tubing and thus contaminate the sample. Such connections and tubing are further described in U.S. patent application Ser. No. 13/206,873 (published as US 2012/0024411), the contents of which are incorporated herein by reference.

In many applications using selector/injector valves to direct fluid flows, and in particular in liquid chromatography, the volume of fluids is small. This is particularly true when liquid chromatography is being used as an analytical method as opposed to a preparative method. Such methods often use capillary columns and are generally referred to as capillary chromatography. In capillary chromatography, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can typically be expressed as those involving fluid flow rates of about 0.5 ml/minute or less.

As noted, liquid chromatography (as well as other analytical instrument) systems typically include several components. For example, such a system may include a pump, an injection valve or autosampler for injecting the analyte, a precolumn filter to remove particulate matter in the analyte solution that might clog the column, a packed bed to retain irreversibly adsorbed chemical material, the LC column itself, and a detector that analyzes the carrier fluid as it leaves the column. Ion chromatography may also utilize a suppressor column to facilitate detection dynamic range. These various components may typically be connected by a miniature fluid conduit, or tubing, such as metallic or polymeric tubing (for ion chromatography), usually having an internal diameter of 0.003 to 0.040 inch.

Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. The reliability and performance of threaded fluidic fittings is dependent on the amount of torque applied to tighten (or loosen) the fittings. Methods and systems for controlling the torque applied to fittings have been described in U.S. Provisional Patent Application Nos. 61/609,795 and 61/723,163, the contents of which are herein incorporated by reference.

It will be understood by those skilled in the art that, as used herein, the term "LC system" is intended in its broad sense to include all apparatus and components in a system used in connection with a liquid chromatography system (including but not limited to HPLC or UHPLC), and that the discussion of components in the context of LC systems is exemplary, as the invention may apply beyond LC systems to gas and ion chromatography, as well as in vitro diagnostic (IVD) or environmental analysis, and in other analytical instruments (AI) and systems, and may be made of only a few simple components or made of numerous, sophisticated components which are computer controlled or the like. Those skilled in the art will also appreciate that an LC system is one type of an AI system. For example, gas chromatography is similar in many respects to liquid chromatography, but obviously involves a gas sample to be analyzed. Although the following discussion focuses on liquid chromatography, those skilled in the art will appreciate that much of what is said with respect to LC systems also has application to gas chromatography, ion chromatography, and other types of AI systems and methods. Other such AI systems and methods may include, for example, lab on a chip, printing, sensors, micro chromatography, biochemical detection, mass spectrometry, biological sensing, drug discovery, drug delivery, molecular separation, proteomics, fuel cells, optics and opto-fluidics, and research tools.

Increasing pressure requirements in liquid chromatography have necessitated the use of high pressure fluidic components. For many applications regular stainless steel tubing is typically used to withstand the high pressure, such as those in excess of 12,000 psi or so. However, for some types of analyses (e.g., biological testing and metal/ion analysis), stainless steel or other metals are not desired in the fluid path as the metal could interfere with the testing. For example, some methods use corrosive salts which can be incompatible with steel, and the stainless steel can react at an ion level with the chemicals used in the mobile phase of separation. Additionally, there are some fields of use (e.g., nano-scale or nano-volume analysis), that require very small inside diameters to accommodate the extremely low volumes required by these applications. Such small inside diameters are typically not available in stainless steel or other high pressure tubing. Traditional materials utilized for instruments targeting biochemistry and ion chemistry have been PEEK and fluoropolymer (e.g., PTFE, ETFE, PFA, FEP, and PCTFE). However, such materials are limited in pressure capability by the yield strength of the material.

SUMMARY OF THE INVENTION

The present disclosure overcomes one or more deficiencies of the prior art by providing a connector with a passageway that is both structurally reinforced and biocompatible. The present disclosure includes a connector for use with an analytical instrument (AI) system. The connector has both a reinforcement insert and a biocompatible molding covering portions of the reinforcement insert. The reinforcement insert provides structural strength to the connector, while the molding provides biocompatibility. Applicants have found that certain embodiments can withstand operating pressures above 12,000 psi, and even operating pressures above 25,000 psi. The reinforcement insert has a first portion, a second portion, and a middle portion between the first and second portion. In the preferred embodiment, both the first portion and the second portion of the reinforcement insert have an interior threaded section, a first interior non-threaded section, and a second interior non-threaded section. In the preferred embodiment, in each of the first and second portions, the junction of the first interior non-threaded section and the second interior non-threaded section forms an interior lip. The middle portion has an interior surface and an exterior surface, and the middle portion defines a plurality of holes. In the preferred embodiment, a biocompatible molding covers the second interior non-threaded section of each of the first portion and the second portion, and the biocompatible molding defines a passageway through the first portion, the second portion, and the middle portion. In certain embodiments, the biocompatible molding has two tapered sections, two non-tapered sections, and an annular projection connecting a first non-tapered section with a second non-tapered section. In certain embodiments, the biocompatible molding covers the exterior surface of the middle portion. In certain embodiments, the biocompatible molding is made from PEEK, and the interior geometry of the molding can be shaped with core pins.

The reinforcement insert and biocompatible molding can be used as a union, an adapter, a tee, a cross, a manifold, or as other fittings or components of an AI system. In certain embodiments, the exterior surface of the first portion or the second portion are hexagonal, while in other embodiments, the exterior surface is round, knurled, or square. In other embodiments, the middle portion of the reinforcement insert has a first interior non-tapered section adjacent to the first portion second interior non-threaded section, a first interior tapered section connected to the middle portion first interior non-tapered section, a second interior non-tapered section adjacent to the second portion second interior non-threaded section, a second interior tapered section connected to the middle portion second interior non-tapered section, and a middle portion interior annular projection between the middle portion first interior tapered section and the middle portion second interior tapered section. In certain embodiments, the middle portion interior annular projection is a biocompatible tube.

DETAILED DESCRIPTION

Figure 1:
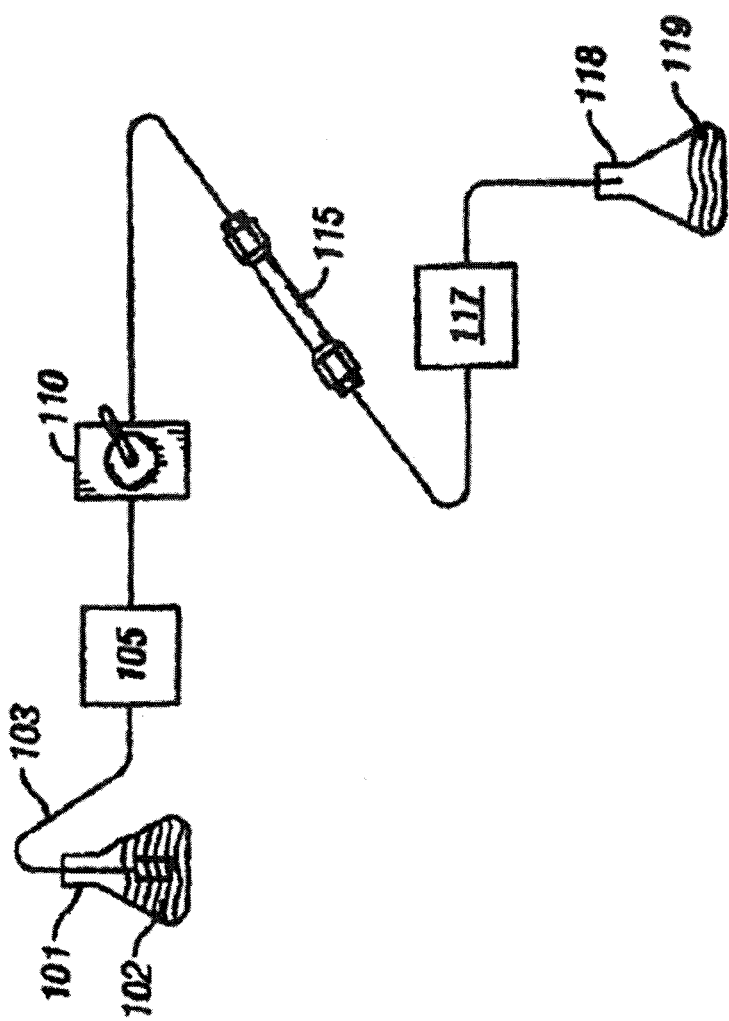
FIG. 1. A block diagram of a conventional liquid chromatography system.

In FIG. 1, a block diagram of certain elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system (which includes HPLC and UHPLC), other analytical instrument (AI) systems can be used in connection with various embodiments of the invention, such as a mass spectrometry, microflow chromatography, nanoflow chromatography, nano-scale liquid chromatography, capillary electrophoresis, or reverse-phase gradient chromatography system.

Figure 2:
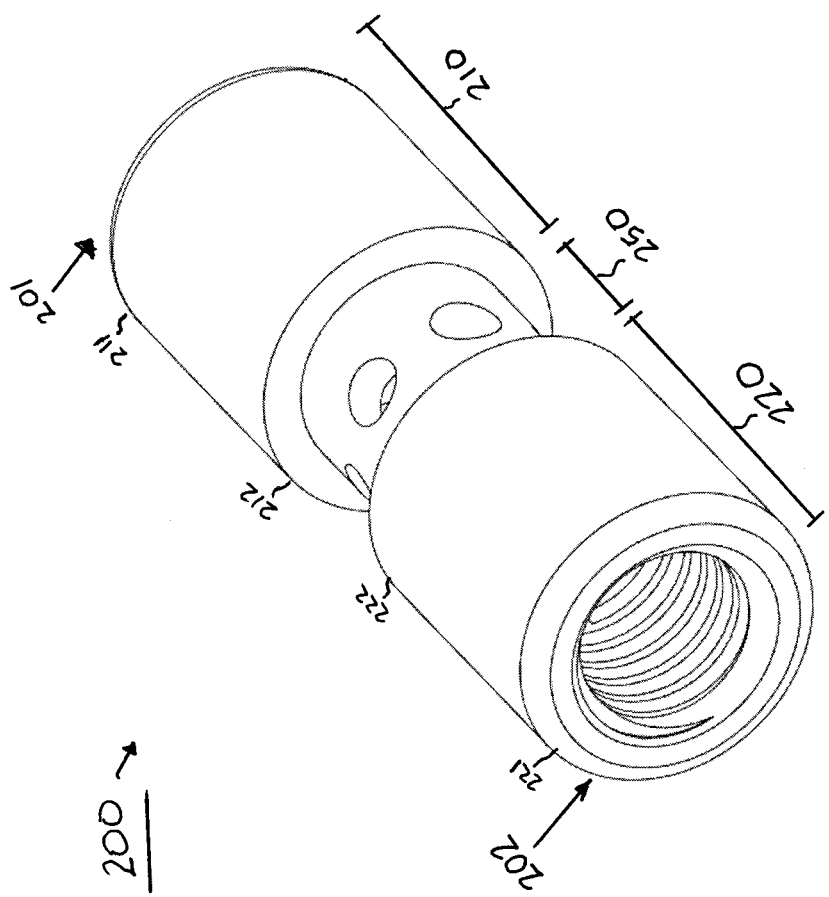
FIG. 2. A perspective view of a union reinforcement insert.
Figure 3:
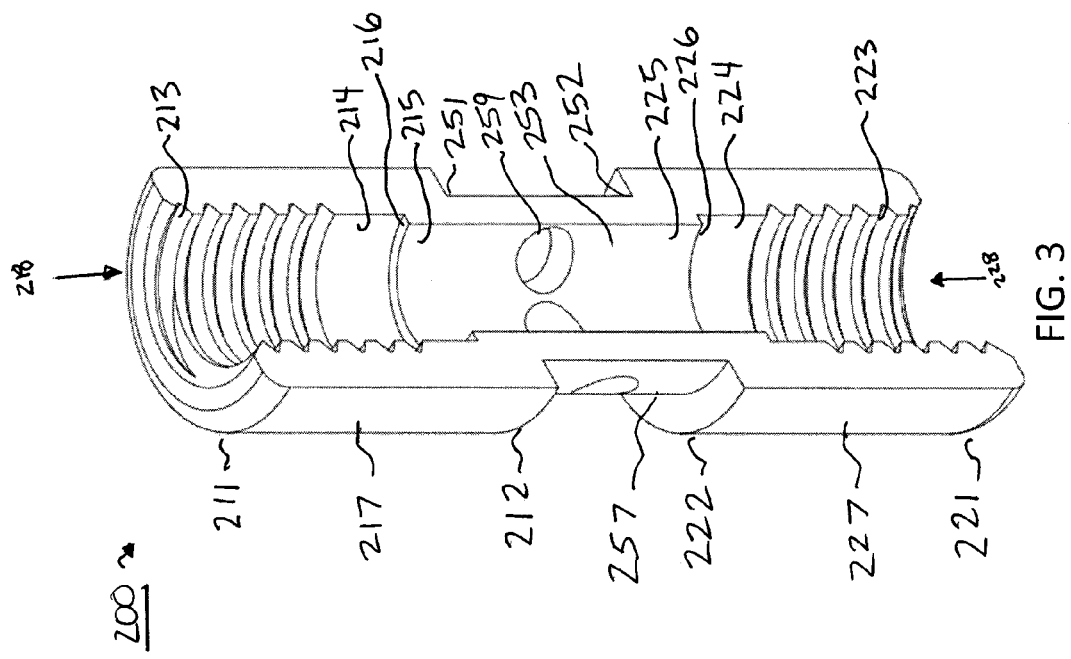
FIG. 3. A sectional side view of the union reinforcement insert of FIG. 2.
Figure 4:
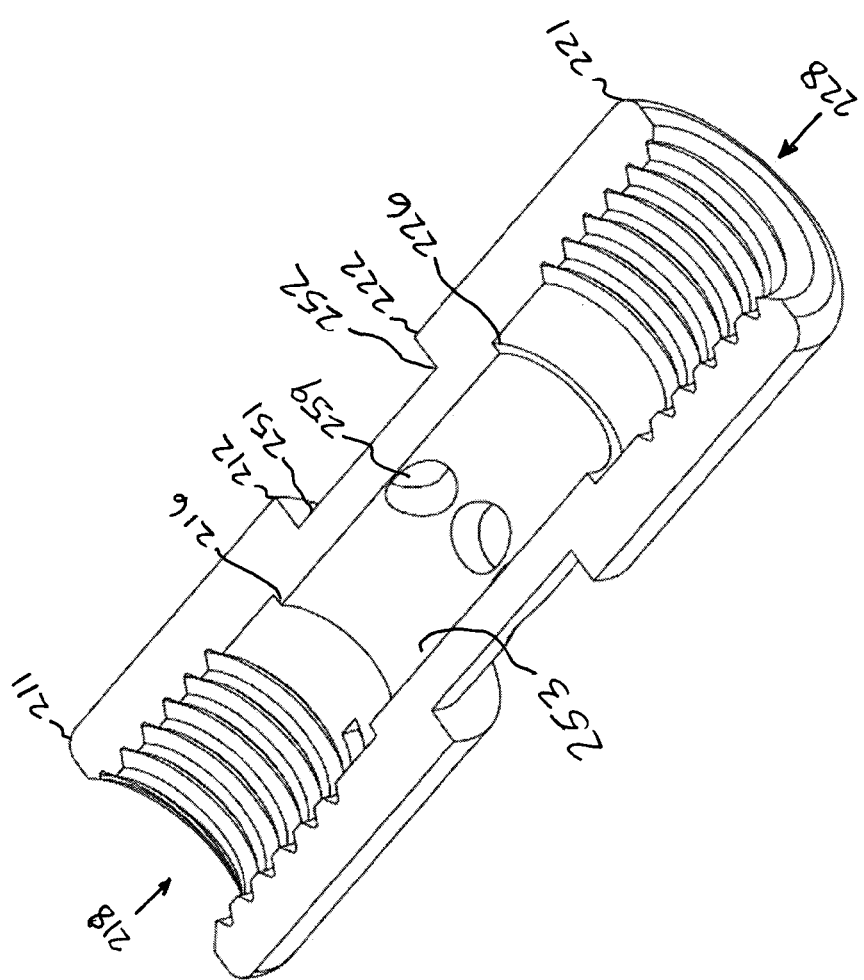
FIG. 4. A perspective sectional view of the embodiment of FIG. 2.

Referring now to FIG. 2, a perspective view of a union reinforcement insert is shown. FIGS. 3 and 4 show a side sectional view and a perspective sectional view, respectively, of the union reinforcement insert of FIG. 2. In one embodiment, reinforcement insert 200 is manufactured with stainless steel, which provides strength for a composite design. However, those of skill in the art will appreciate that other materials can be considered for construction of the reinforcement insert, such as aluminum, titanium, ceramic, or carbon-fiber reinforced PEEK. Ceramics may include, for example, aluminum oxide, zirconium oxide, and yttrium-stabilized zirconium oxide. Reinforcement 200 can be manufactured by machining, casting then machining, or similar processes. Reinforcement insert 200 has a first end 201 and a second end 202 distally located with respect to one another. Reinforcement insert 200 also has a first portion 210 located proximal to the first end 201, a second portion 220 located proximal to the second end 202, and a middle portion 250 located between the first portion 210 and the second portion 220. In the embodiment shown in FIGS. 2-4, the first portion 210 and second portion 220 have substantially identical geometry, though those of skill in the art will appreciate that they can form the first portion 210 and second portion 220 with differing geometries, such as by making one or both of the portions tapered. In the embodiment shown in FIGS. 2-4, the middle portion 250 is in the shape of a groove, which advantageously helps an operator couple a wrench to the reinforcement insert 200, though those of ordinary skill in the art will appreciate that they can design and/or construct the middle portion 250 with a similar outer diameter and geometry as the first portion 210 or second portion 220. The first portion 210 has a first end 211 and a second end 212. The first end 201 of reinforcement 200 is proximal to the first end 211 of the first portion 210. The first portion has an interior threaded section 213 proximal to the first end 211 of the first portion 210, a first interior non-threaded section 214 connected to the first interior threaded section 213, a second interior non-threaded section 215 connected to the first interior non-threaded section 214, and an exterior surface 217. The junction of the first interior non-threaded section 214 and the second interior non-threaded section 215 forms an interior lip 216.

Still referring to FIGS. 2-4, the second portion 220 of reinforcement insert 200 has a first end 221 and a second end 222. The second end 202 of reinforcement 200 is proximal to the first end 221 of the first portion 220. The second portion 220 has an interior threaded section 223 proximal to the first end 221 of the second portion 220, a first interior non-threaded section 224 connected to the interior threaded section 223, a second interior non-threaded section 225 connected to the first interior non-threaded section 224, and an exterior surface 227. The junction of the first interior non-threaded section 224 and the second interior non-threaded section 225 forms an interior lip 226. As will be described later, interior lip 226 and interior lip 216 serve as a shut-off to prevent molded material from flowing into threaded sections 223 and 213, respectively, of reinforcement insert 200.

Still referring to FIGS. 2-4, the middle portion 250 has a middle portion first end 251 adjacent to the first portion second end 212, a middle portion second end 252 adjacent to the second portion second end 222, a middle portion interior surface 253 located between the first portion second interior non-threaded section 215 and the second portion second interior non-threaded section 225, and an exterior surface 257.

Still referring to FIGS. 2-4, the first portion 210 has a passageway 218 between the first portion first end 211 and the first portion second end 212. The second portion 220 has a passageway 228 between the second portion first end 221 and the second portion second end 222. The middle portion has a passageway 258 (not labeled in figures) between the middle portion first end 251 and the middle portion second end 252. In the embodiment shown in FIGS. 2-4, the passageways 218, 228, and 258 are located collinearly with respect to one another along the longitudinal axis of the reinforcement insert 200. In the embodiment shown in FIGS. 2-4, the exterior surfaces 217, 227, and 257 are generally smooth, but those of skill in the art will appreciate that other textures can be used, such as rough or knurled.

Still referring to FIGS. 2-4, middle portion 250 has six injection holes 259 of substantially the same size, fluidly coupled to passageways 258 (not labeled), 218, and 228. In the embodiment shown in FIGS. 2-4, the six injection holes are equally spaced around the circumference of middle portion 250, centered between middle portion first end 251 and middle portion second end 252, and generally perpendicular to passageway 258. In designing and adjusting an injection mold process, as further discussed below, those skilled in the art will appreciate that they may adjust the hole pattern, such that, for example: fewer or more injection holes are used; the holes may be of different sizes; the holes need not be centered between the middle portion ends 251 and 252; and the holes may be placed in multiple rows, staggered, or offset. Further, those of ordinary skill in the art will appreciate that the holes need not be strictly circular, but that the holes can include other forms of openings, such as slots.

Those of skill in the art will appreciate that the lengths and diameters of the various portions and sections of reinforcement insert 200 can be adjusted depending on the size of tubing 103, fittings, and other components of an LC or other AI system. For example, those of skill in the art will appreciate that they can use various thread sizes in the first portion interior threaded section 213 and second portion interior threaded section 223. In the embodiment shown in FIGS. 2-4, the first portion 210, second portion 220, and middle portion 250 are each generally cylindrical in shape. Those of skill in the art will appreciate that other geometries for the portions can be selected, such as hexagonal, knurled, or square and the like.

Figure 5:
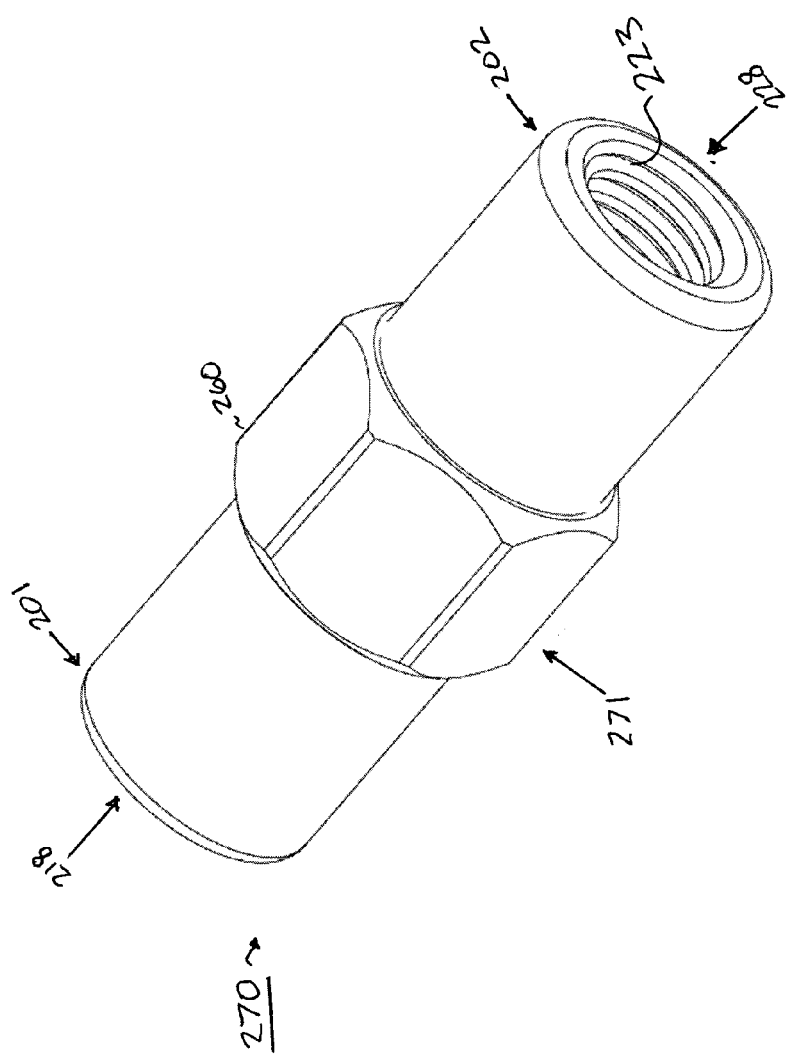
FIG. 5. A perspective view of a biocompatible union in accordance with the embodiment of FIG. 2.
Figure 6:
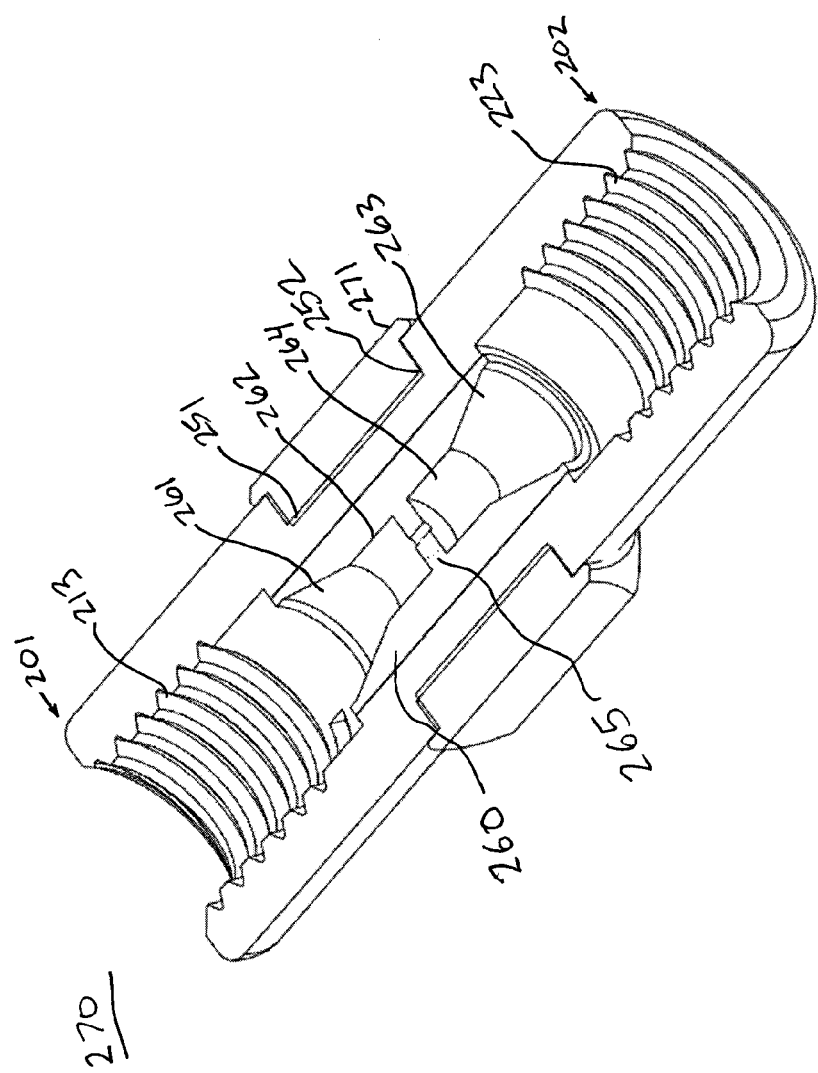
FIG. 6. A perspective sectional view of the embodiment of FIG. 5.

Referring to FIGS. 5 and 6, a perspective view and a perspective sectional view, respectively, of a biocompatible union is shown. Referring to FIGS. 2-6, biocompatible union 270 is fabricated by injecting molded material 260 into reinforcement insert 200. Molded material 260 radially enters reinforcement insert 200 through the middle portion injection holes 259, between the middle portion first end 251 and the middle portion second end 252. The molded material 260 then meets inside of the reinforcement insert 200 along with core pins (not shown) from a fitting engagement (e.g., cones or flat bottom) to form the interior geometry of union 270. The interior geometry of union 270 has first tapered section 261 located proximal to the first portion second interior non-threaded section 215, and a first non-tapered section 262 connected to the first tapered section 261. The interior geometry of union 260 also has a second tapered section 263 located proximal to the second portion second interior non-threaded section 225, and a second non-tapered section 264 connected to the second tapered section 262. The interior geometry of union 270 further has an annular projection 265 located between the first non-tapered section 262 and the second non-tapered section 264. A molded material passageway 268 (not labeled) is located within annular projection 265 and is either molded by the core pins, or machined as a secondary operation through processes known to those of skill in the art, such as drilling, punching, broaching, and EDM. The molded material passageway 268, the first tapered section 261, the first non-tapered section 262, the second tapered section 263, the second non-tapered section 264, and the annular projection 265 are fluidly coupled with one another. The exterior geometry 271 of union 270 is created from a mold cavity.

Figure 7:
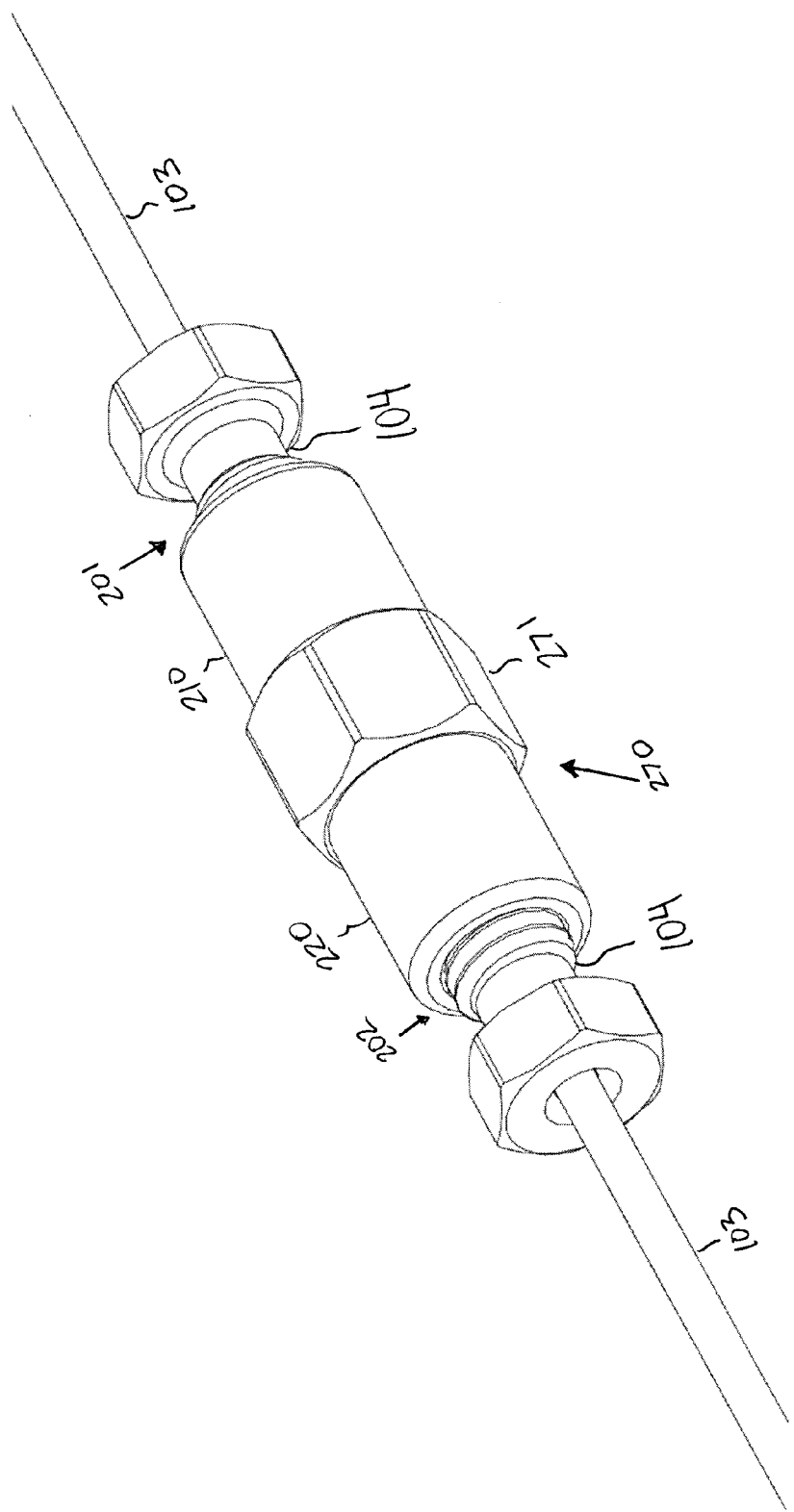
FIG. 7. A perspective view of the biocompatible union of FIGS. 5 and 6 coupled to tubing.

Referring to FIG. 7, a perspective view of a biocompatible union coupled to tubing is shown. As shown in the embodiment of FIG. 7, the exterior geometry 271 of union 270 allows an operator to tighten or loosen union 270 (e.g., by wrench, hand, machine, etc.) and/or to hold union 270 in place while a fitting 104 and tubing 103 are coupled to the union 270. In the embodiment of FIG. 7, exterior geometry 271 is generally hexagonal in shape, though those of skill in the art will appreciate that other shapes can be used, such as square or knurled. Fittings 104 can be coupled to the reinforcement first end 201 and second end 202 via the first portion threaded section 213 and second portion threaded section 223, respectively. In the embodiment of FIG. 7, the coupling of fitting 104 to union 270 occurs through the relatively strong materials found in the reinforcement 200 (e.g., stainless steel, steel titanium, etc.).

Figure 8:
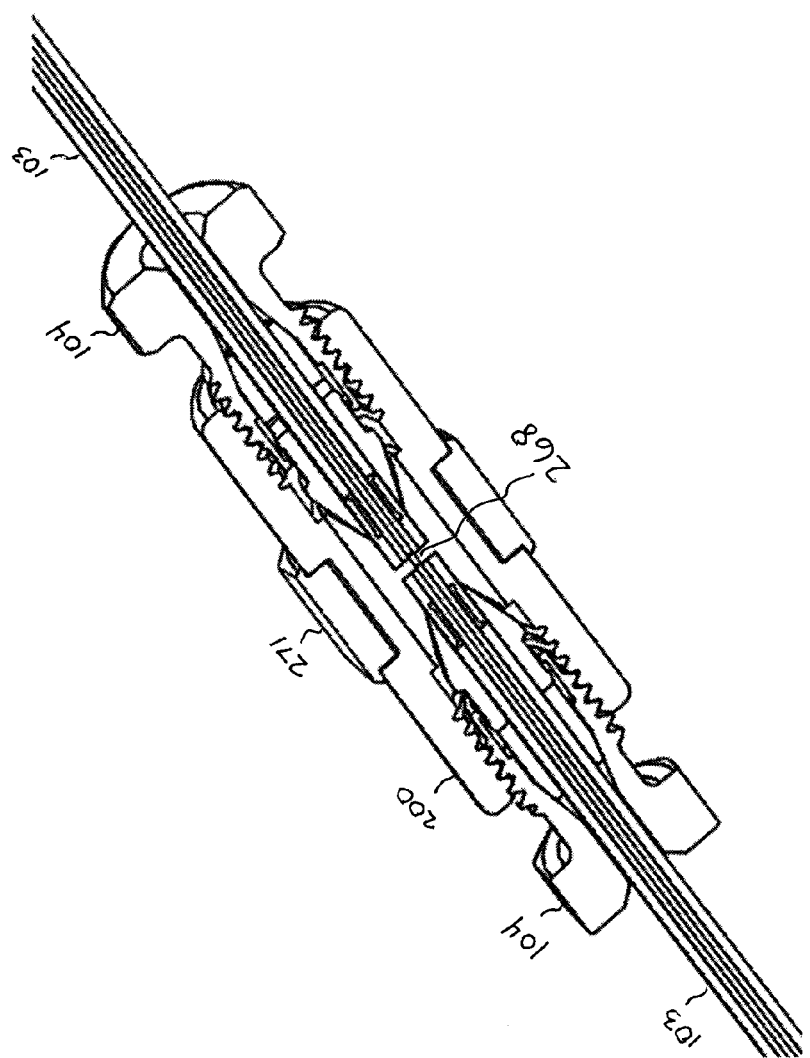
FIG. 8. A perspective sectional view of the embodiment of FIG. 7.

Referring to FIG. 8, a perspective sectional view of the biocompatible union and tubing of FIG. 7 is shown. As shown in FIG. 8, the molded material 260 and passageway 268 are formed such that liquid flowing through biocompatible union 270 is not exposed to the reinforcement insert 200, but is instead exposed to the molded material 260. For an analytical instrument (AI) system (such as LC, which includes HPLC and UHPLC) to be biocompatible, the various components that may come into contact with the effluent or sample to be analyzed are made of polymer in the preferred embodiment. One such polymer that is generally biocompatible and can be used for molded material 260 is polyetheretherketone, which is commercially available under the trademark "PEEK" from Victrex®. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications, such as polytetrafluoroethylene (PTFE, such as TEFLON®), perfluoroalkoxy (PFA, also called perfluoroalkoxyethylene), fluorinated ethylene propylene (FEP), ethylene tetrafluoroethylene (ETFE, available as TEFZEL®), polychlorotrifluoroethylene (PCTFE), polyetherimide (PEI), polyphenylene sulfide (PPS), polypropylene, sulfone polymers, polyolefins, polyimides, other polyaryletherketones, polyoxymethylene (POM, such as DELRIN®), and others, depending on the process conditions.

Figure 9:
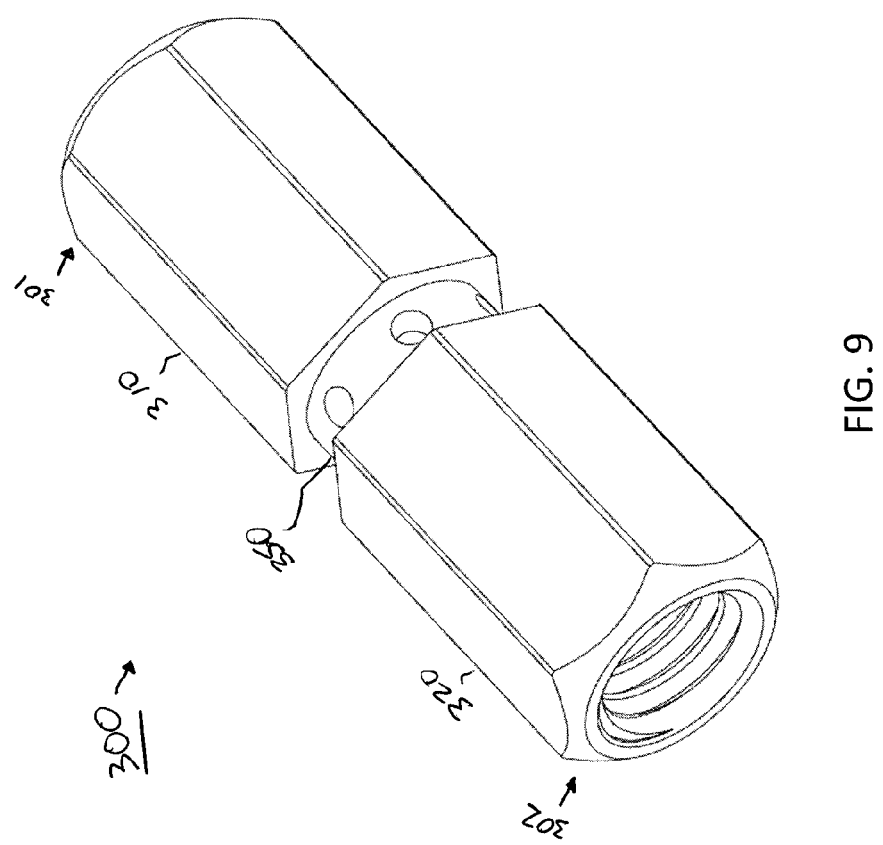
FIG. 9. A perspective view of an alternative embodiment of a union reinforcement insert.
Figure 10:
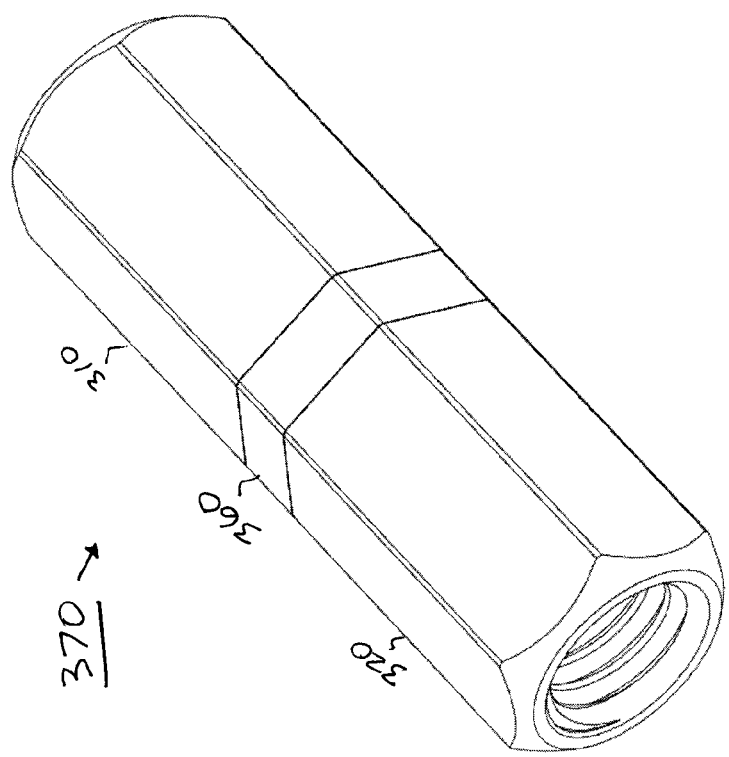
FIG. 10. A perspective view of a biocompatible union in accordance with the embodiment of FIG. 9.

Referring now to FIG. 9, a perspective view is shown of an alternative embodiment of a union reinforcement insert. Reinforcement insert 300 has a first end 301 and a second end 302 distally located with respect to one another. Reinforcement insert 300 also has a first portion 310 located proximal to the first end 301, a second portion 320 located proximal to the second end 302, and a middle portion 350 located between the first portion 310 and the second portion 320. Reinforcement insert 300 is substantially identical to reinforcement insert 200, except that the first portion 310 and the second portion 320 of reinforcement insert 300 are generally hexagonal in shape, while the first portion 210 and second portion 220 of reinforcement insert 200 are generally cylindrical in shape. Referring to FIG. 10, a perspective view is shown of a biocompatible union is shown according to the embodiment of FIG. 9. Union 370 is fabricated by injecting molded material 360 into reinforcement insert 300.

Figure 11:
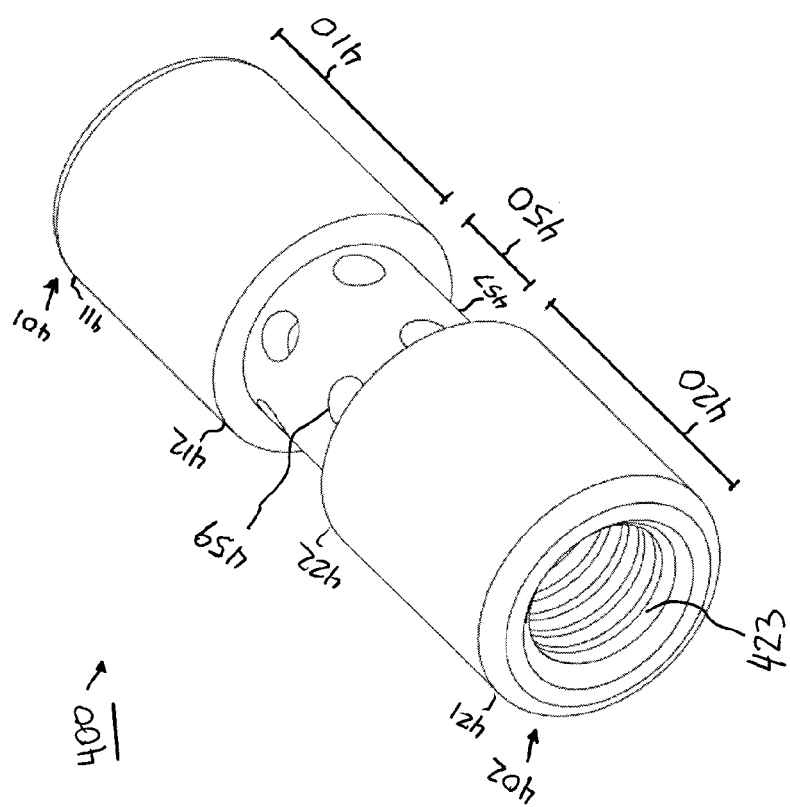
FIG. 11. A perspective view of a union reinforcement insert with an interior reinforcement web.
Figure 12:
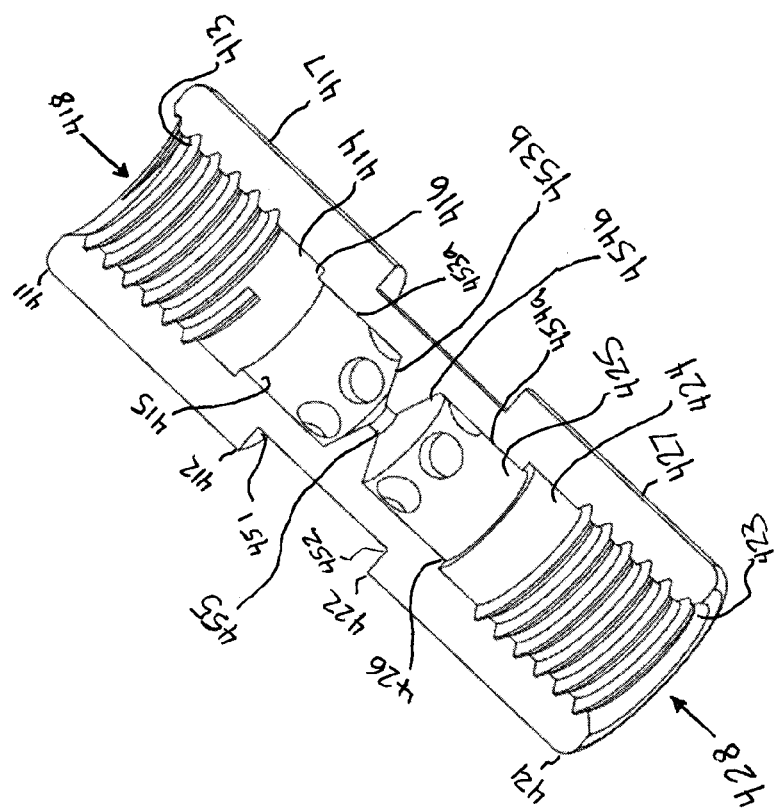
FIG. 12. A perspective sectional view of the embodiment of FIG. 11.

Referring now to FIGS. 11 and 12, a perspective view and a perspective sectional view, respectively, of an embodiment of a union reinforcement insert with an interior reinforcement web is shown. In the embodiment of FIGS. 11 and 12, reinforcement insert 400 has a first end 401 and a second end 402 distally located with respect to one another. Reinforcement insert 400 also has a first portion 410 located proximal to the first end 401, a second portion 420 located proximal to the second end 402, and a middle portion 450 located between the first portion 410 and the second portion 420. In the embodiment shown in FIGS. 11 and 12, the first portion 410, second portion 420, and middle portion 450 are each generally cylindrical in shape. In the embodiment shown in FIGS. 11-12, the first portion 410 and second portion 420 have substantially identical geometries, though those of skill in the art will appreciate that they can form the first portion 210 and second portion 220 with differing geometries, such as by making one or both of the portions tapered. In the embodiment shown in FIGS. 11 and 12, the middle portion 450 is in the shape of a groove, which advantageously helps an operator couple a wrench to the reinforcement insert 400, though those of ordinary skill in the art will appreciate that they can design and/or construct the middle portion 450 with a similar outer diameter and geometry as the first portion 410 or second portion 420.

The first portion 410 has a first end 411 and a second end 412. The first end 401 of reinforcement insert 400 is proximal to the first end 411 of the first portion 410. The first portion has an interior threaded section 413 proximal to the first end 411 of the first portion 410, a first interior non-threaded section 414 connected to the first interior threaded section 413, a second interior non-threaded section 415 connected to the first interior non-threaded section 414, and an exterior surface 417. The junction of the first interior non-threaded section 414 and the second interior non-threaded section 415 forms an interior lip 416.

Still referring to FIGS. 11-12, the second portion 420 of reinforcement insert 400 has a first end 421 and a second end 422. The second end 402 of reinforcement insert 400 is proximal to the first end 421 of the first portion 420. The second portion 420 has an interior threaded section 423 proximal to the first end 421 of the second portion 420, a first interior non-threaded section 424 connected to the interior threaded section 423, a second interior non-threaded section 425 connected to the first interior non-threaded section 424, and an exterior surface 427. The junction of the first interior non-threaded section 424 and the second interior non-threaded section 425 forms an interior lip 426. The interior lip 426 and interior lip 416 serve as a shut-off to prevent molded material from flowing into threaded sections 423 and 413, respectively, of reinforcement insert 400.

Still referring to FIGS. 11-12, the middle portion 450 has a middle portion first end 451 adjacent to the first portion second end 412 and a middle portion second end 452 adjacent to the second portion second end 422. Middle portion 450 also has a middle portion first interior non-tapered section 453a located adjacent to the first portion second interior non-threaded section 415, a middle portion first interior tapered section 453b connected to the middle portion first interior non-tapered section 453a, a middle portion second interior non-tapered section 454a located adjacent to the second portion second interior non-threaded section 425, a middle portion second interior tapered section 454b connected to the middle portion second interior non-tapered section 454a, a middle portion interior annular projection 455 located between (and connected to) the middle portion first interior tapered section 453b and the middle portion second interior tapered section 454b. Middle portion 450 also has an exterior surface 457.

Still referring to FIGS. 11-12, the first portion 410 has a passageway 418 between the first portion first end 411 and the first portion second end 412. The second portion 420 has a passageway 428 between the second portion first end 421 and the second portion second end 422. The middle portion has a passageway 458 (not labeled) between the middle portion first end 451 and the middle portion second end 452, fluidly coupling the middle portion first interior non-tapered section 453a, the middle portion first interior tapered section 453b, the middle portion second interior non-tapered section 454a, the middle portion second interior tapered section 454b, and the middle portion interior annular projection 455. In the embodiment shown in FIGS. 11-12, the passageways 418, 428, and 458 are located collinearly with one another along the longitudinal axis of the reinforcement insert 400.

Still referring to FIGS. 11 and 12, middle portion 450 has twelve injection holes 459 of substantially the same size, fluidly coupled to passageways 458, 418, and 428. In the embodiment shown in FIGS. 11 and 12, the injection holes 459 are arranged into two rows with six injection holes in each row, and within each row the injection holes 459 are equally spaced around the circumference of middle portion 450 and generally perpendicular to passageway 458. In the embodiment shown in FIGS. 11 and 12, one set of six injection holes is located proximal to the middle portion first interior non-tapered section 453a, and one set of six injection holes is located proximal to the middle portion second interior non-tapered section 454a. Those skilled in the art will appreciate that they may adjust the hole pattern, such that, for example: fewer or more injection holes are used; the holes may be of different sizes; the holes need not be perpendicular to the middle portion passageway; and the holes may be placed in multiple rows, staggered, or offset. Further, those of ordinary skill in the art will appreciate that the holes need not be strictly circular, but that the holes can include other forms of openings, such as slots.

Figure 13:
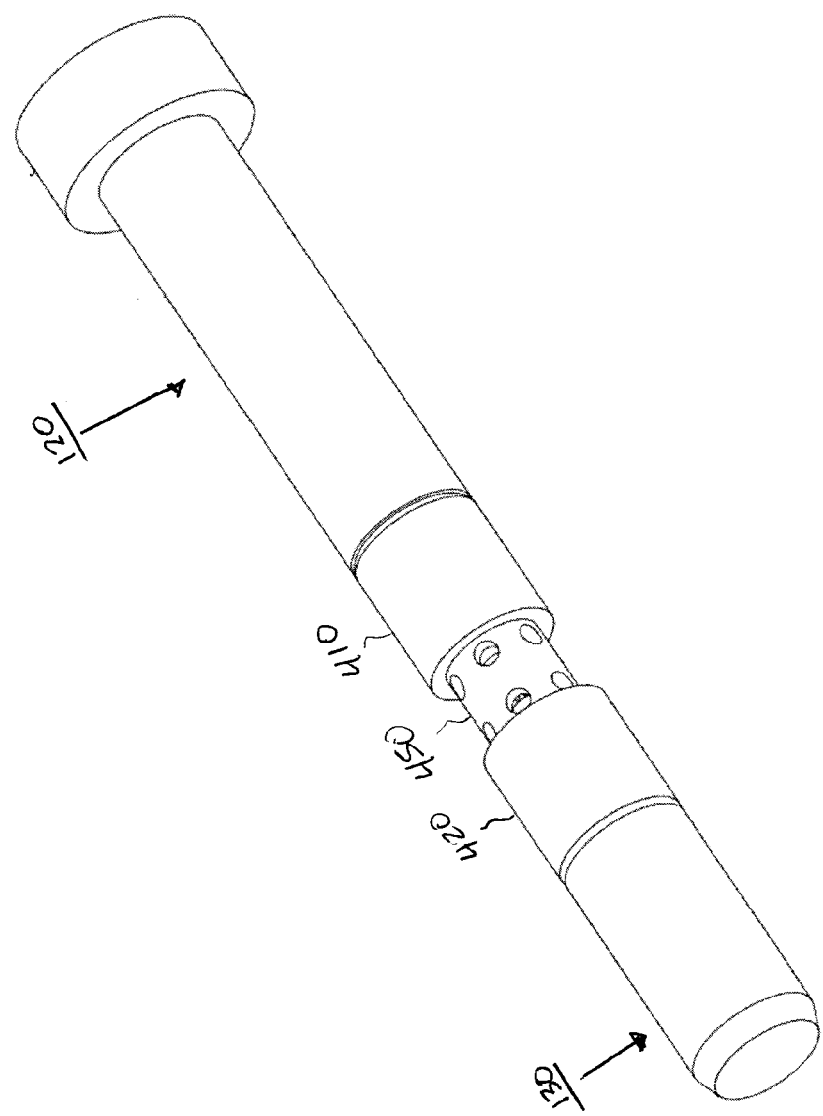
FIG. 13. A perspective view of core pins inserted into the union reinforcement insert of FIGS. 11 and 12.
Figure 14:
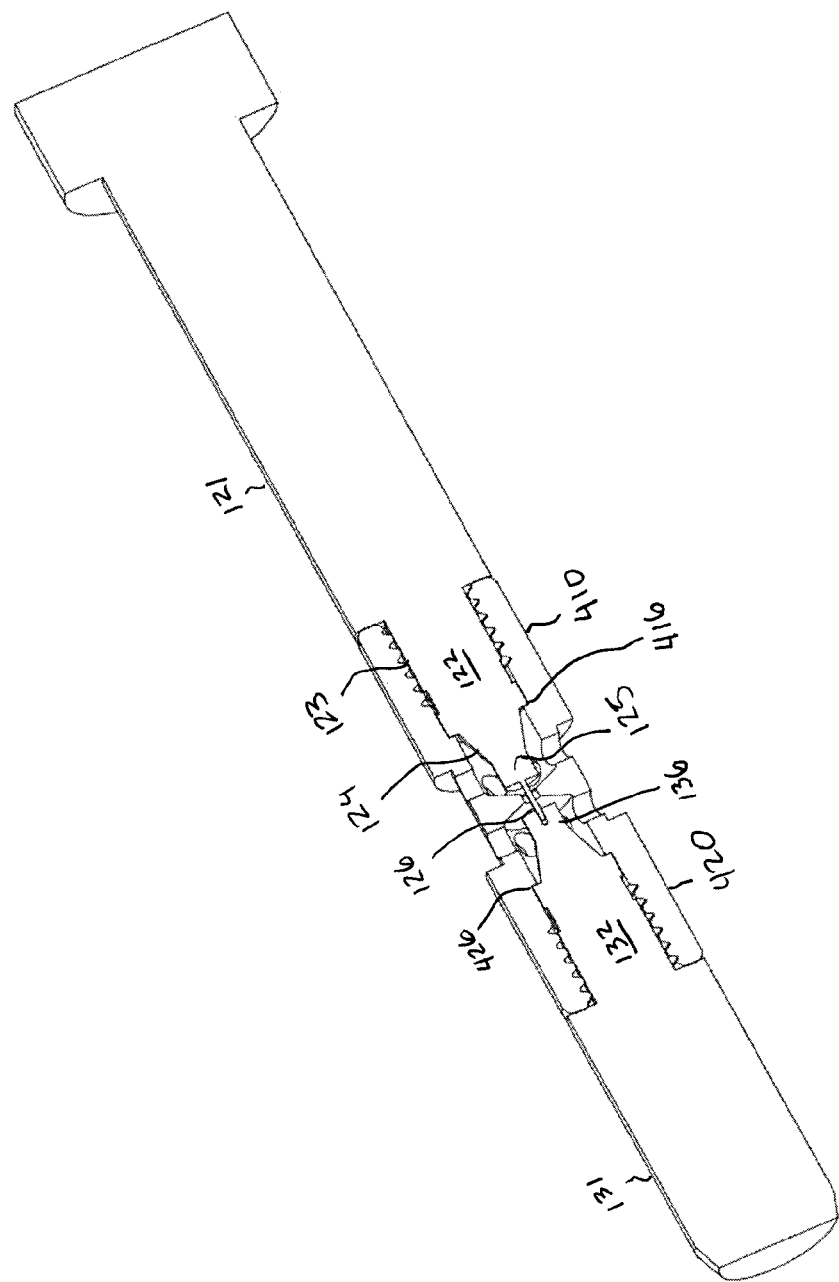
FIG. 14. A perspective sectional view of the embodiment of FIG. 13.

Referring now to FIGS. 13 and 14, a perspective view and a perspective sectional view, respectively, are shown of core pins inserted into the reinforcement insert of FIGS. 11-12. Core pins 120 and 130 are typically made from steel, such as H-13, P-20, A-2, S-7, D-2, and 420-SS. Those of skill in the art will appreciate that they can select the core pin material based on the material to be molded. For example, those of skill in the art may select H-13 core pins to use with PEEK molded material and 420-SS core pins to use with fluoropolymer. Core pin 120 has a head 121 and a body 122, and core pin 130 has a head 131 and a body 132. In the perspective view shown in FIG. 13, only the heads 121 and 131 can be seen. Though the heads 121 and 131 are generally cylindrical, those of skill in the art will appreciate that the core pin heads can be formed in numerous other geometries, such as square, hexagonal, or knurled. As shown in FIG. 14, a core pin body 122 is connected to core pin head 121, and a core pin body 132 is connected to core pin head 131. The core pin body 122 has a first non-tapered section 123 adjacent to head 121, a tapered section 124 connected to the non-tapered section 123, a second non-tapered section 125 connected to the first tapered section 124, and a male port 126 projecting from the second non-threaded section 125. The core pin body 132 has first non-tapered section 133 (not labeled) adjacent to head 131, a tapered section 134 (not labeled) connected to the first non-tapered section 133 (not labeled), a second non-tapered section 135 (not labeled) connected to the first tapered section 134 (not labeled), and a female port 136 located within the second non-tapered section 135 (not labeled).

Referring to FIGS. 11-14, the core pins 120 and 130 are designed such that the reinforcement insert 400 can be slid onto the core pins. In the embodiments of FIGS. 11-14, the core pins 120 and 130 are coupled to and concentrically aligned with reinforcement insert 400. Core pins 120 and 130 are coupled to reinforcement insert 400 by aligning the first non-tapered section 123 of core pin 120 with the first portion interior threaded section 413 of reinforcement insert 400, and by aligning the first non-tapered section 133 of core pin 130 with the first portion interior threaded section 423 of reinforcement insert 400. When core pins 120 and 130 are coupled to the reinforcement insert 400, the male port 126 of core pin 120 extends into the interior annular projection 455 of middle portion 450, and the male port 126 of core pin 120 nests inside the female port 136 of core pin 130. In addition, interior lips 416 and 426 serve as a shut-off between the reinforcement insert 400 and the core pins 120 and 130, respectively, preventing the molded material 460 from flowing into the first portion interior threaded section 413 and the second interior threaded section 423.

Figure 15:
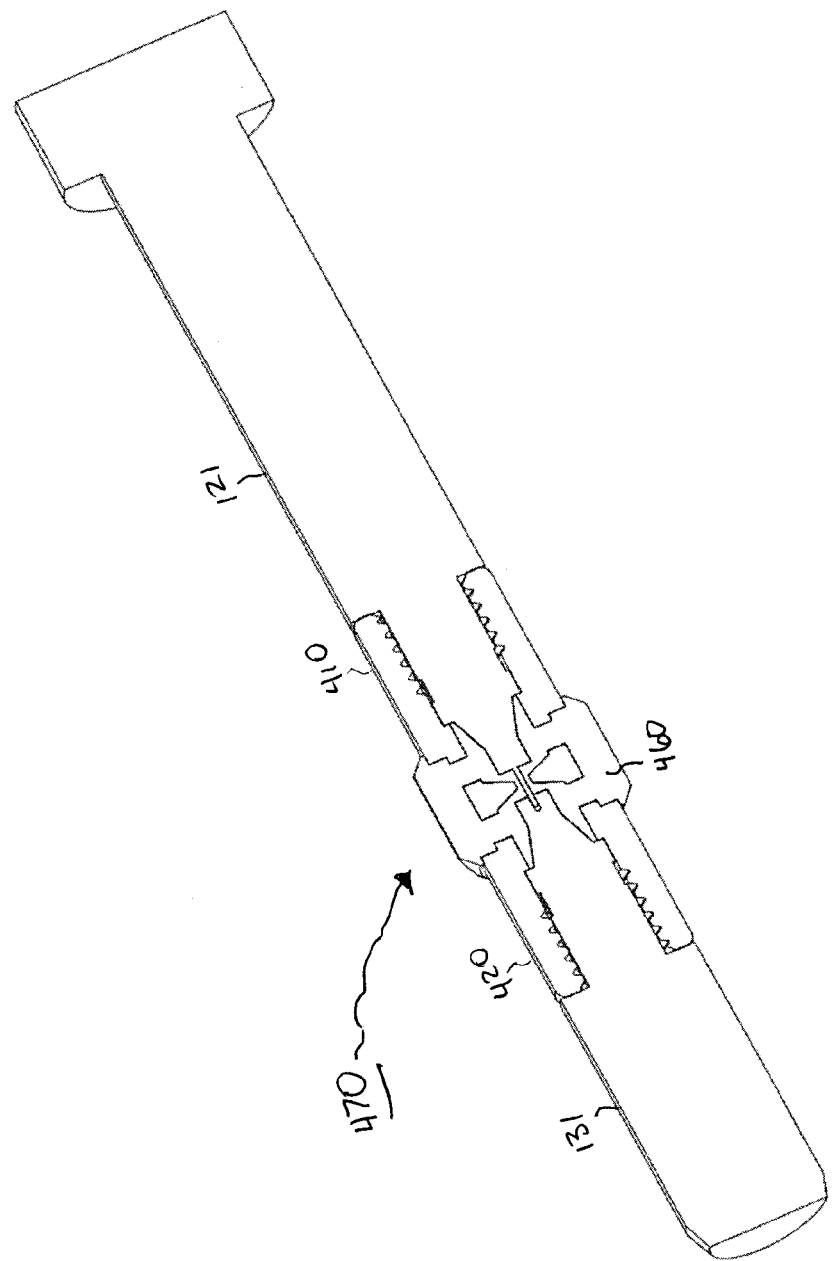
FIG. 15. A perspective sectional view of a biocompatible union with core pins in accordance with the embodiment of FIGS. 13 and 14.
Figure 16:
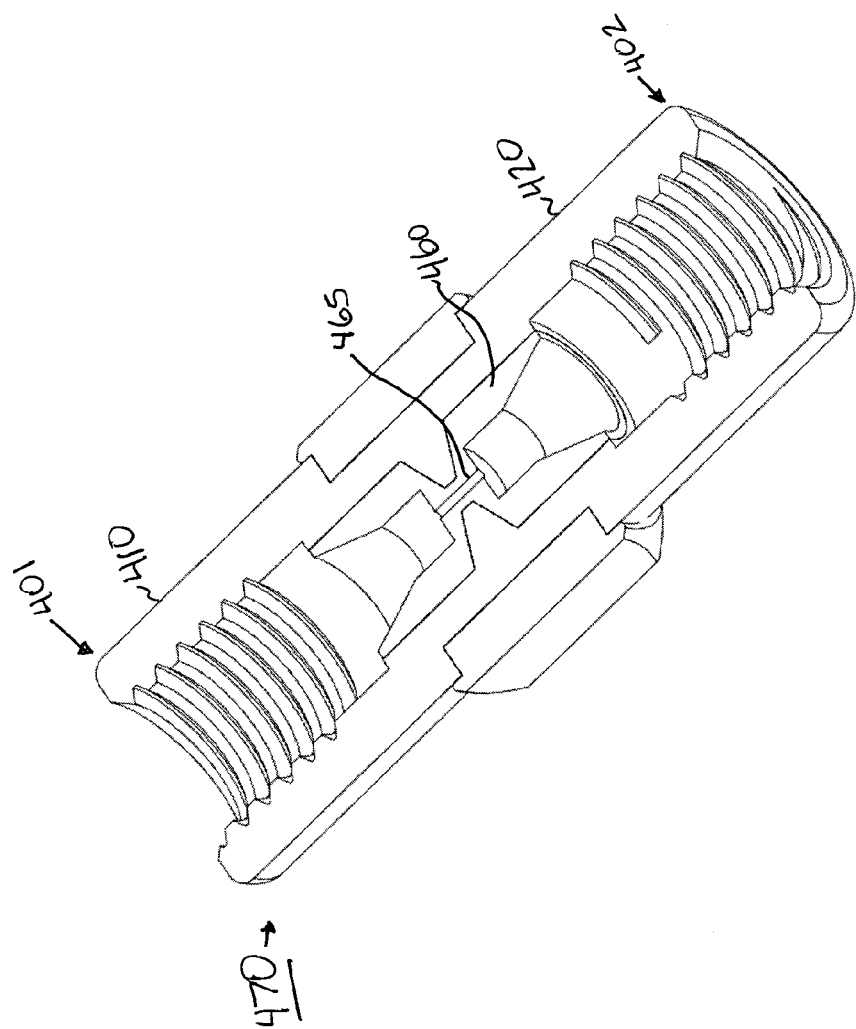
FIG. 16. A perspective sectional view of the embodiment of FIG. 15 with core pins removed.

Referring to FIG. 15, a perspective sectional view of a biocompatible union with core pins is shown. Referring to FIGS. 14-16, biocompatible union 470 is fabricated by injecting molded material 460 into reinforcement insert 400. Molded material 460 radially enters reinforcement insert 400 through the middle portion injection holes 459. The molded material 460 then meets inside of the reinforcement insert 400 along with core pins 120 and 130 (including male port 126 and female port 136) to form the interior geometry of union 470. The interior geometry includes a molded material annular projection 465 located within the reinforcement insert middle portion annular projection 455, and a molded material passageway 468 within the molded material annular projection 465. The exterior geometry of union 470 is created from a mold cavity (not shown).

As compared to biocompatible union 270 (shown in FIGS. 5 and 6), biocompatible union 470 is generally able to withstand increased operating pressures, because the interior reinforcement web provides additional reinforcement. In comparing the embodiment shown in FIGS. 5 and 6 (without interior reinforcement web) with the embodiment shown in FIG. 16 (with interior reinforcement web), molded material annular projection 465 and molded material passageway 468 (which is not labeled, but is located within molded material annular projection 465) are surrounded by additional reinforcement material—e.g., steel, aluminum, titanium, ceramic, or carbon-fiber reinforced PEEK—vis-à-vis middle portion interior annular projection 455. In contrast, molded material passageway 268 is surrounded by molded material 260. Advantageously, the additional reinforcement material present in biocompatible union 470 helps minimize shearing damage to the molded material 460 by stabilizing the linear force transmitted by a tube 103 upon tightening the tube to the biocompatible union 470; this helps prevent damage to the biocompatible union (e.g., failure or leakage) due to overtightening or repeated tightening cycles.

Figure 17:
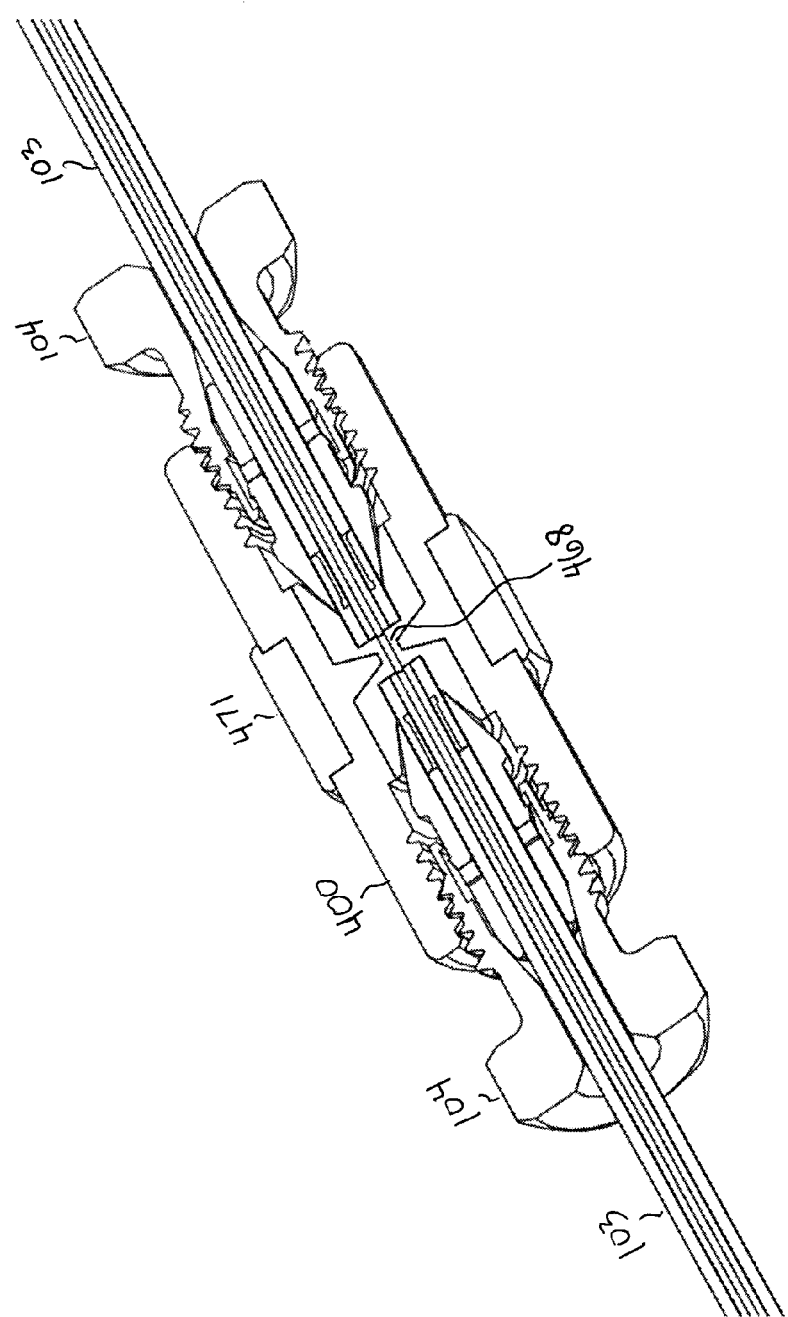
FIG. 17. A perspective sectional view of the embodiment of FIG. 16 coupled to tubing.

Referring to FIG. 17, a perspective sectional view of the biocompatible union of FIG. 16 is shown coupled to tubing. As shown in FIGS. 16 and 17, the molded material 460 and passageway 468 are formed such that liquid flowing through biocompatible union 470 is not exposed to the reinforcement insert 400, but is instead exposed to the molded material 460.

Figure 18:
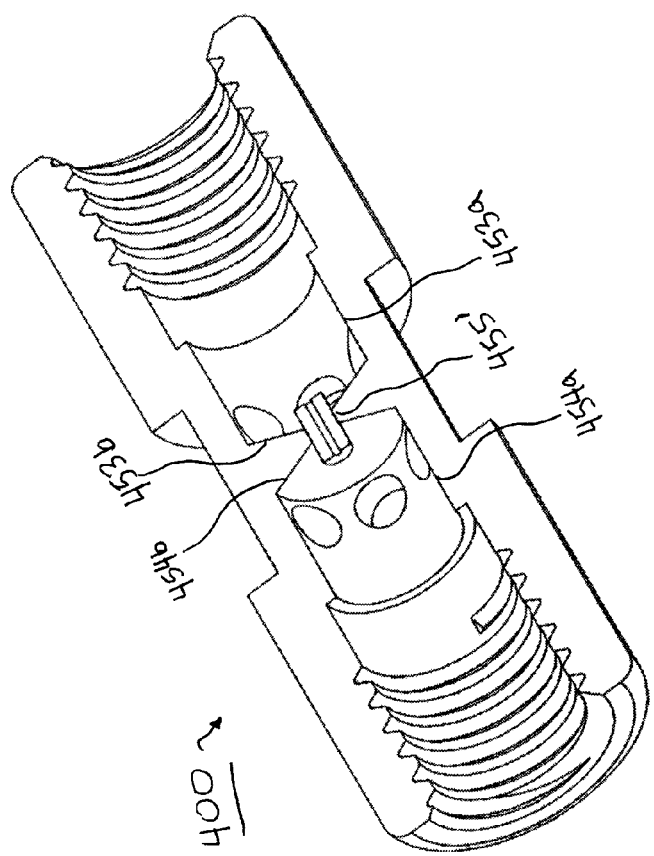
FIG. 18. A perspective sectional view of a union reinforcement insert with a biocompatible tube.

Referring now to FIG. 18, a perspective sectional view is shown of an alternative embodiment of the reinforcement insert shown in FIG. 12. In place of the middle portion annular projection 455 of the embodiment shown in FIG. 12, the alternative embodiment shown in FIG. 18 has a biocompatible tube 455'. Those of skill in the art will appreciate that biocompatible tube 455' can be made from a variety of materials, including PEEK, fluoropolymers (e.g., PTFE, ETFE, FEP, PFA), and can also be made from the same materials used for the molded material 460. Biocompatible tube 455' can be secured to the reinforcement insert 400 through an interference fit with the middle portion first interior tapered portion 453b and the middle portion second interior tapered portion 454b. The biocompatible tube 455' is dimensioned such that sufficient material extends into the first interior non-tapered portion 453a and second interior non-tapered portion 454a in order seal against core pins during molding.

Figure 19:
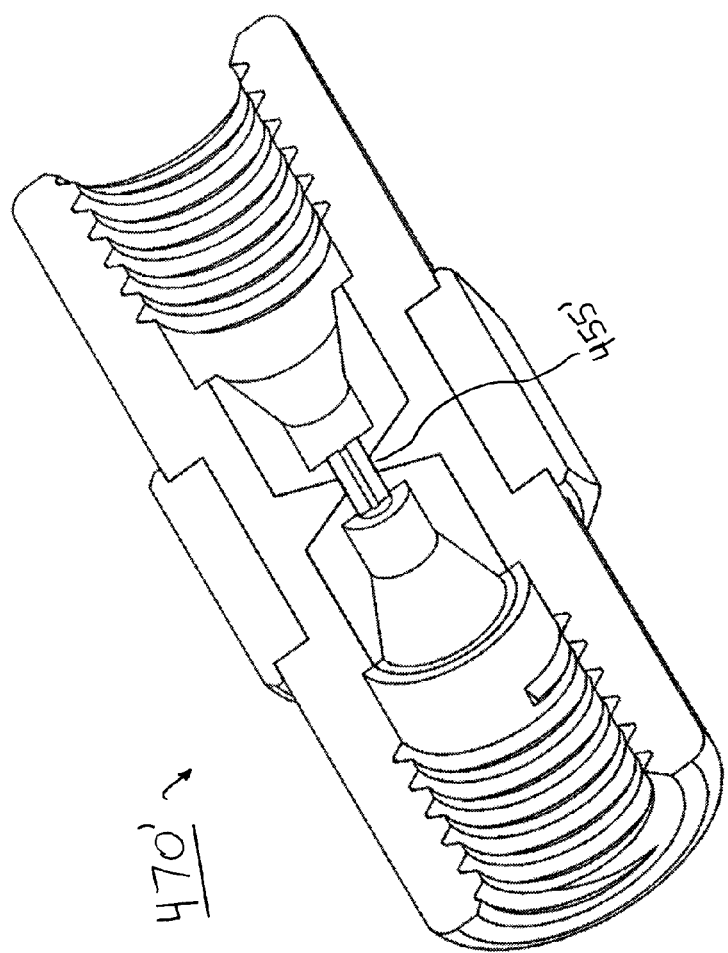
FIG. 19. A perspective sectional view of a biocompatible union in accordance with the embodiment of FIG. 18.

Referring now to FIG. 19, a perspective sectional view of a biocompatible union is shown in accordance with the embodiment of FIG. 18. Biocompatible union 470' is formed when the molded material 460 enters the reinforcement insert 400 with the biocompatible tube 455'. The interior of the biocompatible tube 455' provides a molded material passageway 468 (not labeled). The exterior geometry of the biocompatible union 470' looks the same as the exterior geometry of biocompatible union 470. Advantageously using the biocompatible tube 455' to provide the molded material passageway 468 eliminates deburring operations that are typical when molded material passageways are machined. Further, the biocompatible tube allows for more precise small interior-diameter passageways to be manufactured, such as those in the 25 μm (0.001") to 510 μm (0.020") range.

Figure 20:
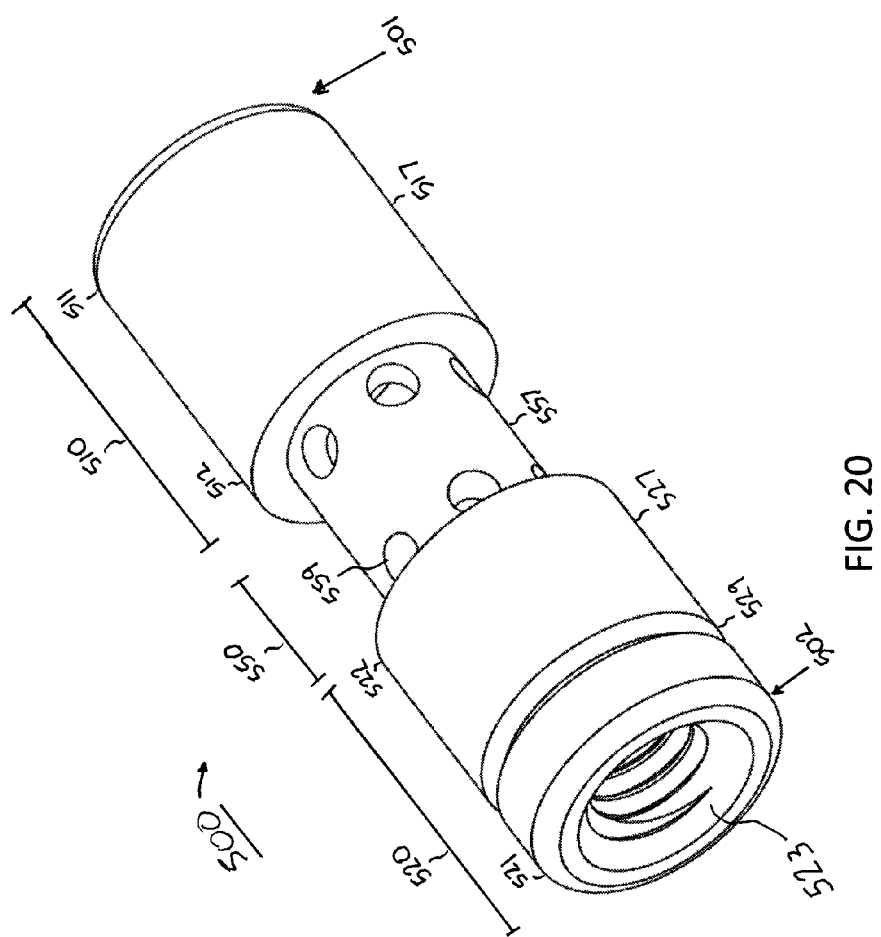
FIG. 20. A perspective view of an adapter reinforcement insert.
Figure 21:
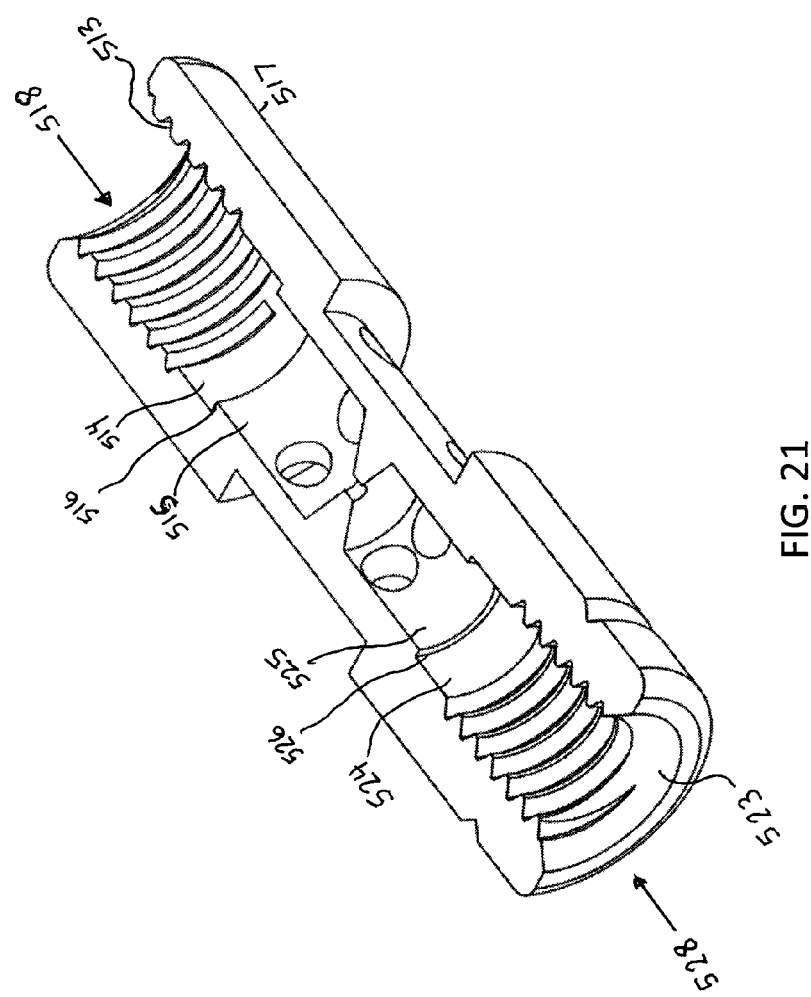
FIG. 21. A perspective sectional view of the embodiment of FIG. 19.

Referring now to FIGS. 20 and 21, a perspective view and a perspective sectional view, respectively, of an adapter reinforcement insert with an interior reinforcement web is shown. Adapter reinforcement insert 500 has a first end 501 and a second end 502 distally located with respect to one another. Reinforcement insert 500 also has a first portion 510 located proximal to the first end 501, a second portion 520 located proximal to the second end 502, and a middle portion 550 located between the first portion 510 and the second portion 520. In the embodiment shown in FIGS. 20 and 21, the first portion 510, second portion 520, and middle portion 550 are each generally cylindrical in shape. The first portion 510 has a first end 511 and a second end 512. The first end 501 of reinforcement insert 500 is proximal to the first end 511 of the first portion 510. The first portion has an interior threaded section 513 proximal to the first end 511 of the first portion 510, a first interior non-threaded section 514 connected to the first interior threaded section 513, a second interior non-threaded section 515 connected to the first interior non-threaded section 514, and an exterior surface 517. The junction of the first interior non-threaded section 514 and the second interior non-threaded section 515 forms an interior lip 516.

Still referring to FIGS. 20 and 21, the second portion 520 of reinforcement insert 500 has a first end 521 and a second end 522. The second end 502 of reinforcement insert 500 is proximal to the first end 521 of the first portion 520. The second portion 520 has an interior threaded section 523 proximal to the first end 521 of the second portion 520, a first interior non-threaded section 524 connected to the interior threaded section 523, a second interior non-threaded section 525 connected to the first interior non-threaded section 524, and an exterior surface 527. The junction of the first interior non-threaded section 524 and the second interior non-threaded section 525 forms an interior lip 526. The interior lip 526 and interior lip 516 serve as a shut-off to prevent molded material from flowing into threaded sections 523 and 513, respectively, of reinforcement insert 500. Reinforcement insert 500 also has a middle portion 550.

Figure 22:
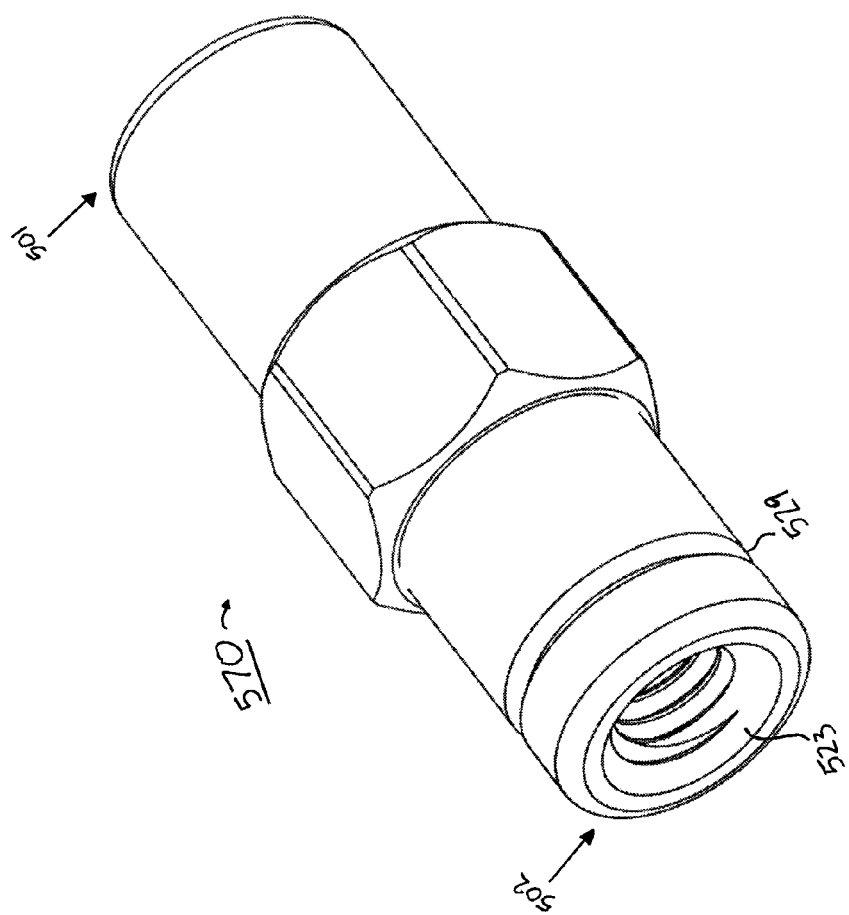
FIG. 22. A perspective view of a biocompatible adapter.
Figure 23:
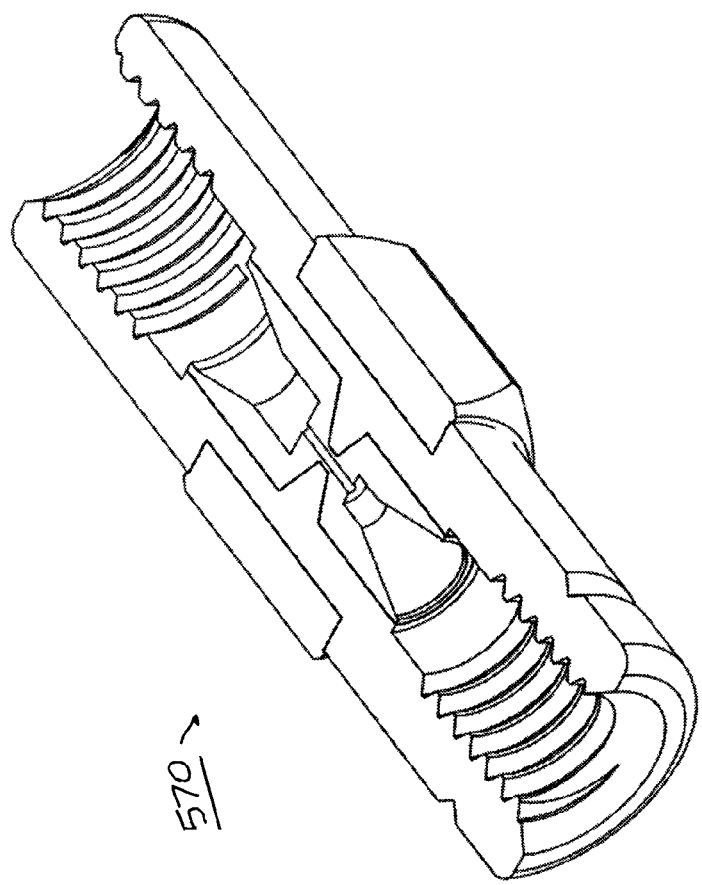
FIG. 23. A perspective sectional view of the embodiment of FIG. 21.

To use the reinforcement insert 500 as an adapter, the interior threaded section 523 of the second portion 520 and the interior threaded section 513 of the first portion 510 can be different, such as a different diameter, angle, lead, or pitch. The exterior surface 527 of reinforcement insert 500 has an exterior lip 529 in the second portion. The exterior lip 529 can function as a visual aid for assembly to indicate the different threading of the second portion 520, as compared to the threading of the first portion 510. Alternatively, those of skill in the art will appreciate that they may identify the different threading in other manners, such as by forming reinforcement insert 500 with a second portion having a reduced outer diameter, by including additional wrench flats, or by stamping the insert to indicate thread size. Referring to FIGS. 22-23, which show a perspective view and a perspective sectional view, respectively, adapter 570 is fabricated by injecting molded material 560 into adapter reinforcement insert 500 using processes similar to those described with respect to the other embodiments.

Figure 24:
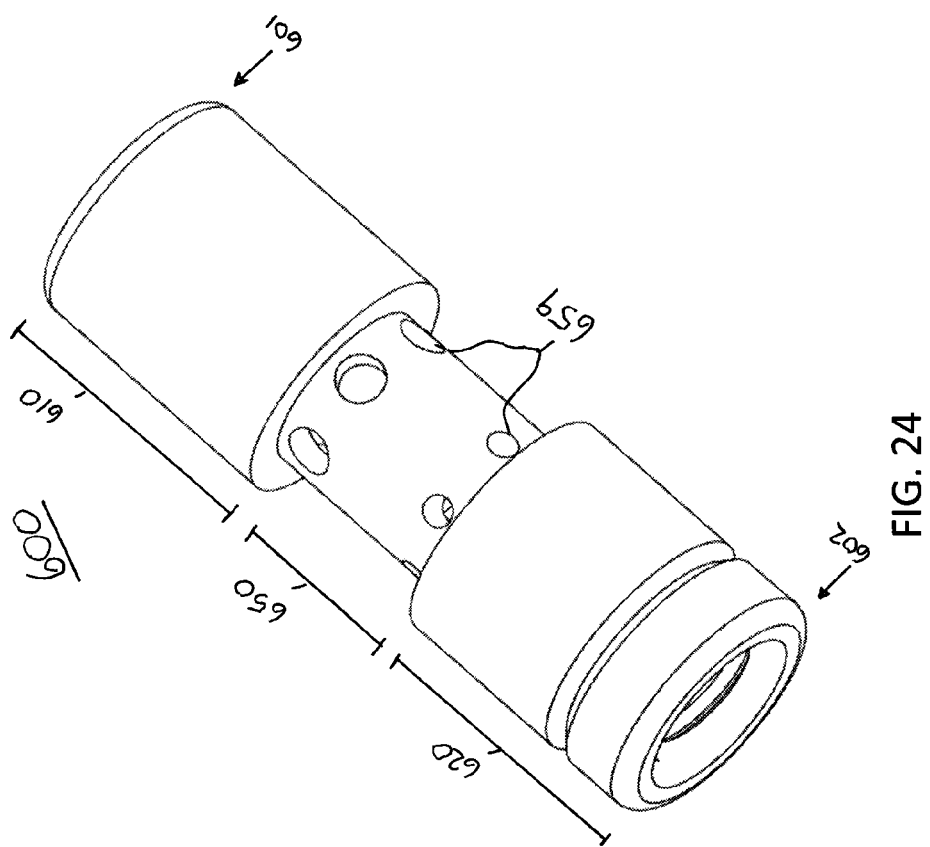
FIG. 24. A perspective view of an alternative embodiment of an adapter reinforcement insert.
Figure 25:
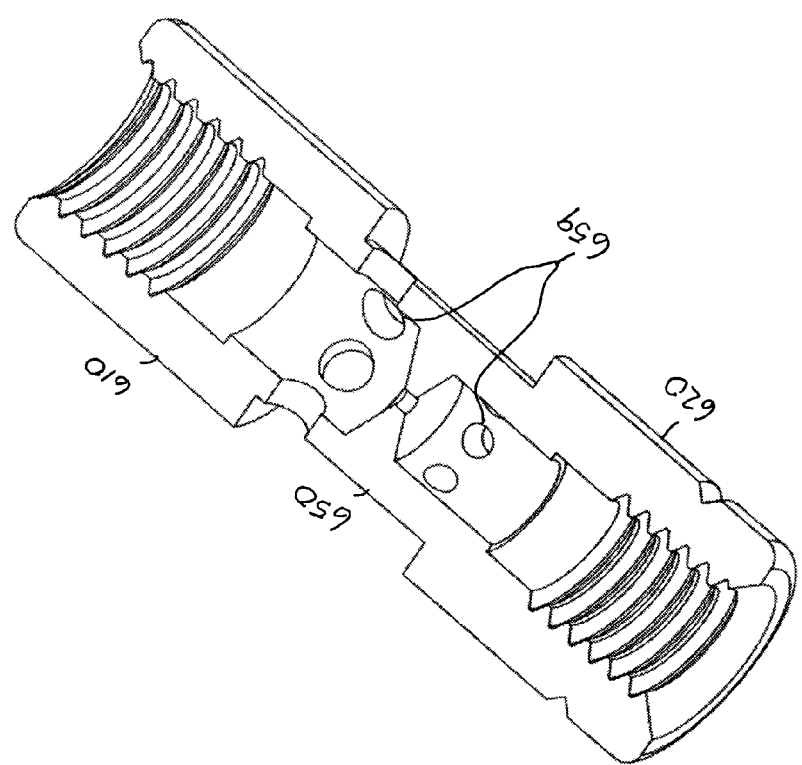
FIG. 25. A perspective sectional view of the embodiment of FIG. 23.

Referring to FIGS. 24 and 25, a perspective view and perspective sectional view, respectively, are shown of an alternative embodiment of an adapter reinforcement insert with an interior reinforcement web. Reinforcement insert 600 has a first end 601 and a second end 602 distally located with respect to one another. Reinforcement insert 600 also has a first portion 610 located proximal to the first end 601, a second portion 620 located proximal to the second end 602, and a middle portion 650 located adjacent to the first portion 610. Reinforcement insert 600 is substantially identical to reinforcement insert 500, except that the injection holes 659 in the middle portion 650 are of different sizes with respect to one another, while the injection holes 559 in the middle portion 550 of reinforcement insert 500 are substantially the same as one another. In the embodiment shown in FIGS. 24 and 25, the injection holes 659 are arranged in two rows with six injection holes in each row. Within each row, the injection holes 659 are equally spaced around the circumference of middle portion 650. The six injection holes in the row nearest the second portion 620 are of a certain diameter, while the six injection holes in the row nearest the first portion 610 are of a larger diameter. Those of skill in the art will appreciate that within a given row, the injection holes need not be of the same shape or diameter. Providing a reinforcement insert with injection holes of different diameters advantageously gives designers and operators additional flexibility in controlling the flow of material into a particular area of the reinforcement insert during molding. For example, those of skill in the art may design injection holes 659 of different diameter to account for non-uniform thickness of molded material, or the inability to have the same number of holes on a particular feature of the insert.

Figure 26:
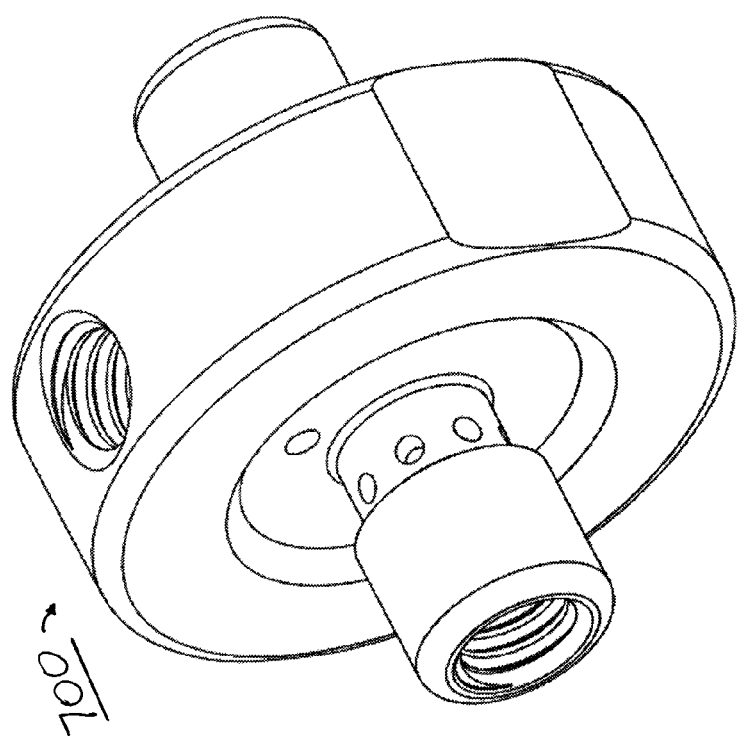
FIG. 26. A perspective view of a tee reinforcement insert.
Figure 27:
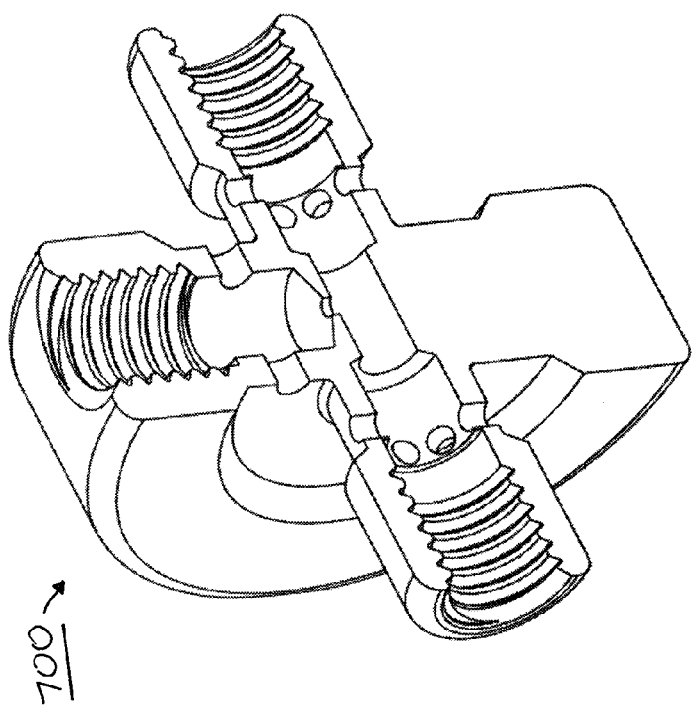
FIG. 27. A perspective sectional view of a tee reinforcement insert.
Figure 28:
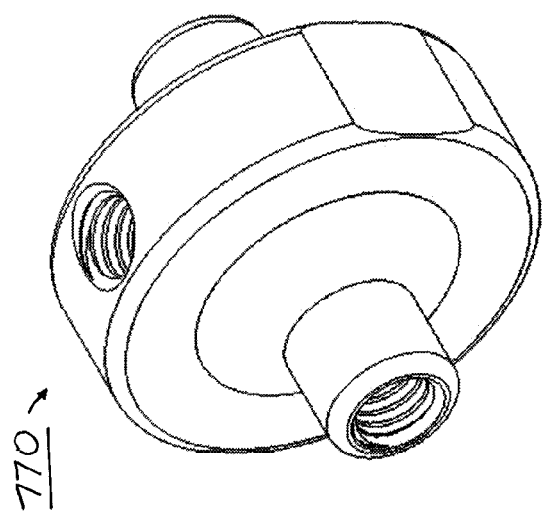
FIG. 28. A perspective view of a biocompatible tee in accordance with the embodiments of FIGS. 26 and 27.
Figure 29:
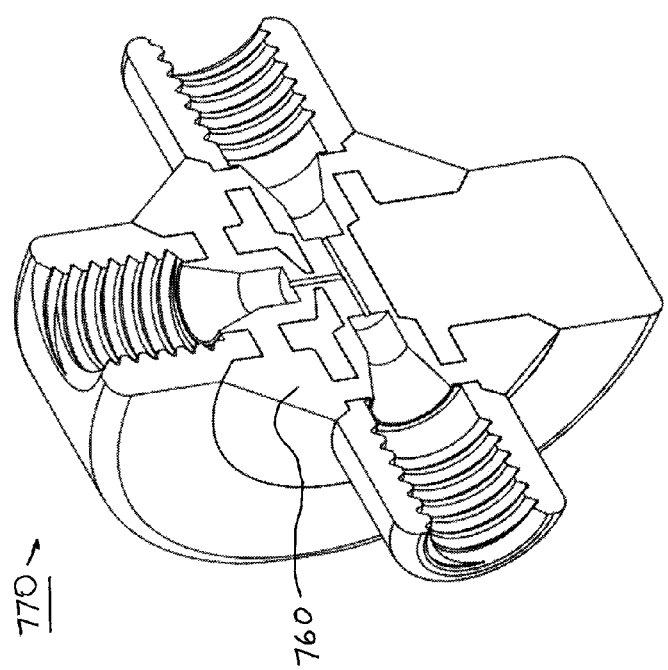
FIG. 29. A perspective sectional view of the embodiment of FIG. 28.

Referring to FIGS. 26 and 27, a perspective view and perspective sectional view, respectively of another embodiment of a reinforcement insert are shown. Reinforcement insert 700 can be used for a "tee." Referring to FIGS. 28 and 29, a perspective view and perspective sectional view, respectively, of a biocompatible tee is shown. Reinforcement insert 700 is formed with interior and exterior geometry using the principles discussed herein with respect to the other embodiments. Biocompatible tee 770 is formed by injecting molded material 760 into reinforcement insert 770, in a similar manner to the processes described in the previous embodiments.

Figure 30:
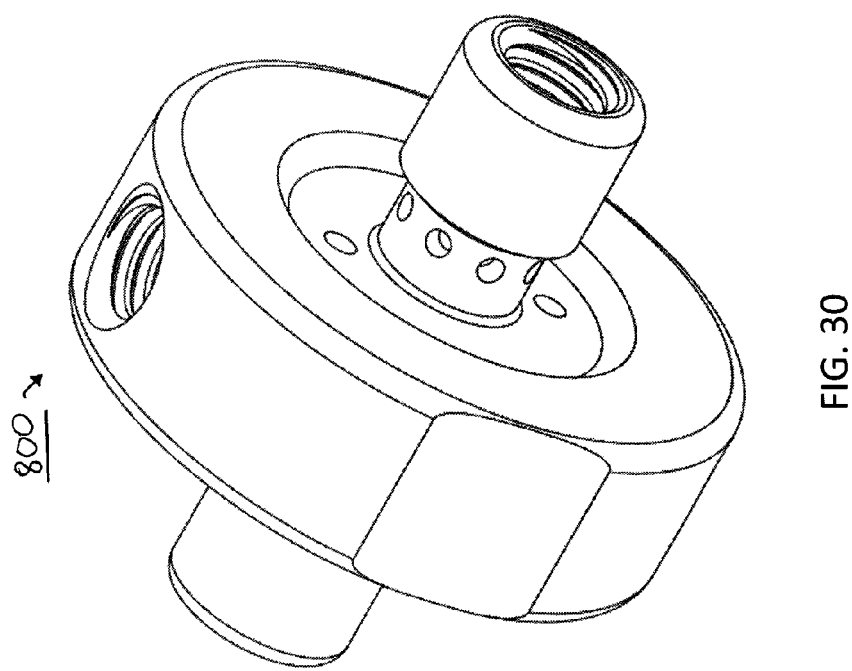
FIG. 30. A perspective view of a cross reinforcement insert.
Figure 31:
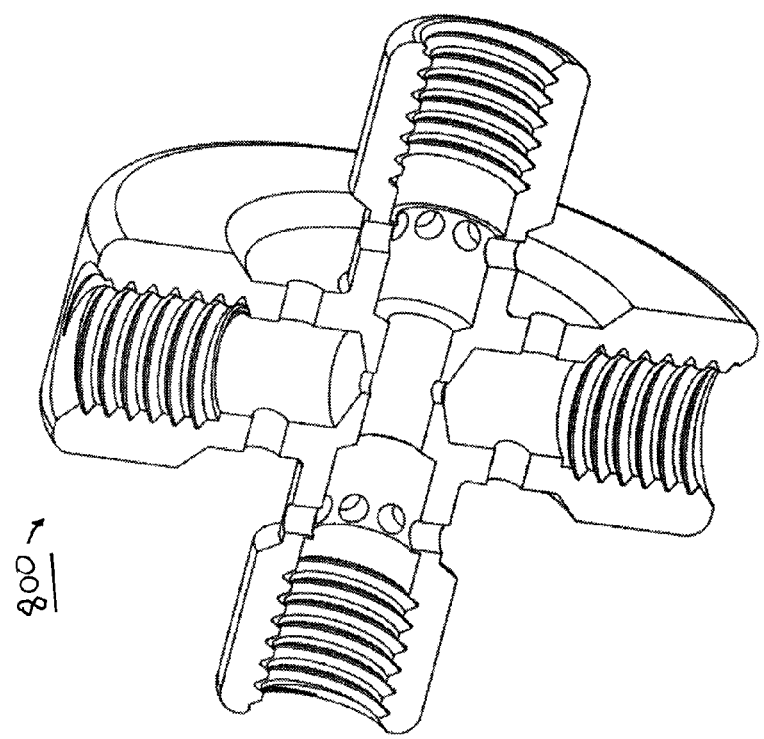
FIG. 31. A perspective sectional view of the embodiment of FIG. 30.
Figure 32:
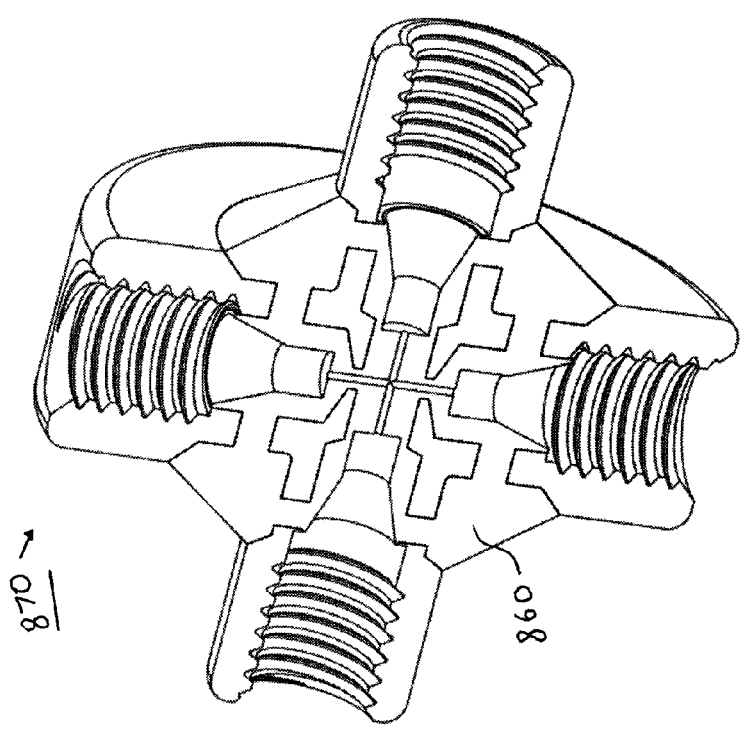
FIG. 32. A perspective sectional view of a biocompatible cross in accordance with the embodiment of FIGS. 30 and 31.

Referring to FIGS. 30 and 31, a perspective view and perspective sectional view, respectively of another embodiment of a reinforcement insert are shown. Reinforcement insert 800 can be used for a cross. Referring to FIG. 32, a perspective view of a biocompatible cross is shown. Biocompatible cross 870 is formed by injecting molded material 800 into reinforcement insert 870, in a similar manner to the processes described in the previous embodiments.

Figure 33:
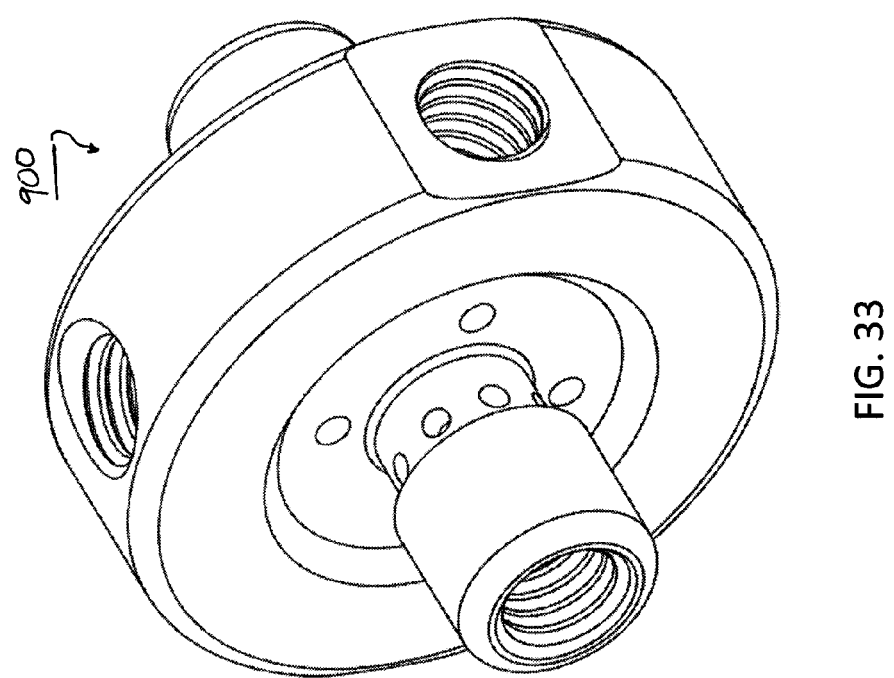
FIG. 33. A perspective view of a manifold reinforcement insert.
Figure 34:
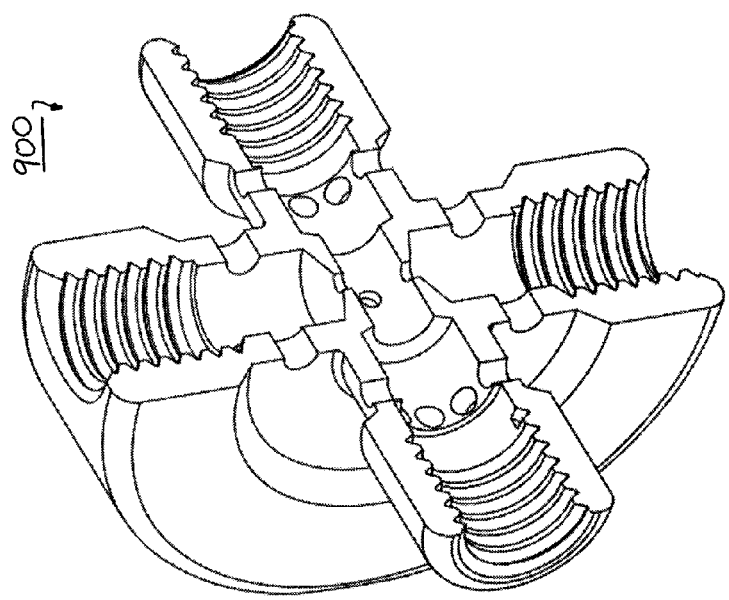
FIG. 34. A perspective sectional view of the embodiment of FIG. 33.
Figure 35:
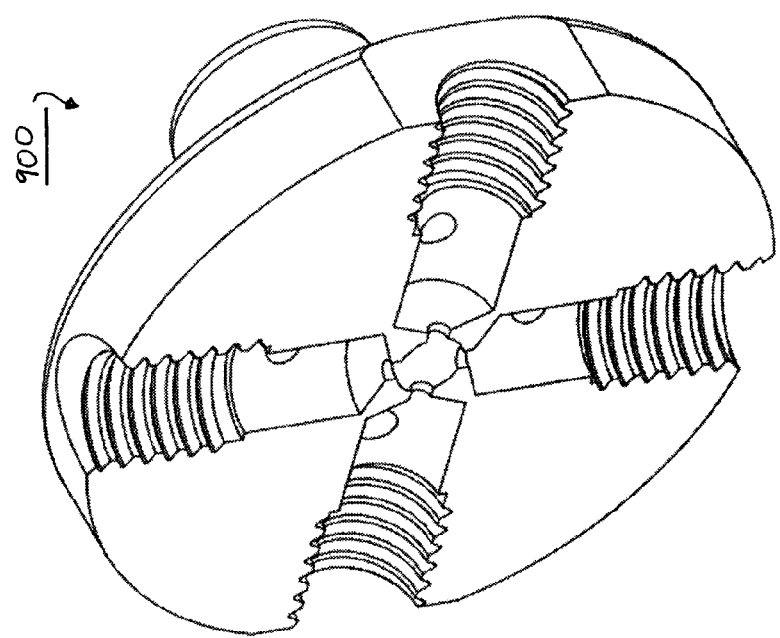
FIG. 35. Another perspective sectional view of the embodiment of FIG. 33.
Figure 36:
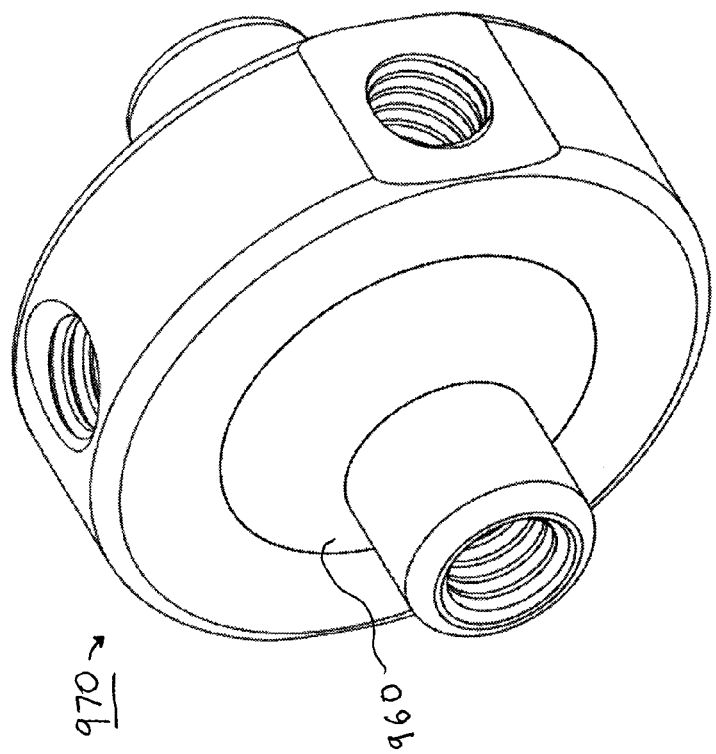
FIG. 36. A perspective view of a biocompatible manifold in accordance with the embodiments of FIGS. 33-35.
Figure 37:
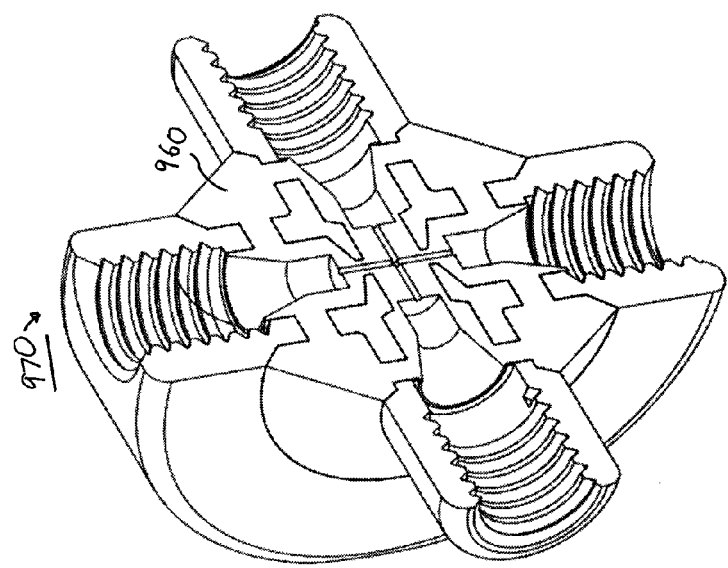
FIG. 37. A perspective sectional view of a biocompatible manifold in accordance with the embodiment of FIG. 34.
Figure 38:
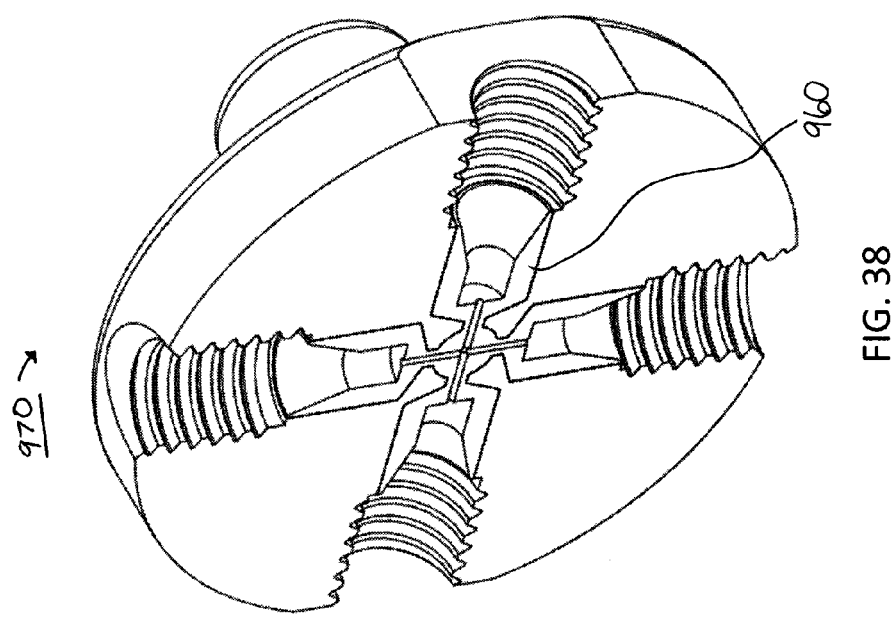
FIG. 38. A perspective sectional view of a biocompatible manifold in accordance with the embodiment of FIG. 35.

Referring to FIGS. 33 and 34-35, a perspective view and two perspective sectional views, respectively of another embodiment of a reinforcement insert are shown. Reinforcement insert 900 can be used for a manifold. Referring to FIGS. 36 and 37-38, a perspective view and perspective sectional view, respectively, of a biocompatible manifold is shown. Biocompatible manifold 970 is formed by injecting molded material 960 into reinforcement insert 970, in a similar manner to the processes described in the previous embodiments.

While the disclosure has shown and described various embodiments, those skilled in the art will appreciate from the drawings and the foregoing discussion that various changes, modifications, and variations may be made without departing from the spirit and scope of the invention as set forth in the claims. For example, those skilled in the art will appreciate that the teachings herein can be used for a wide variety of implementations in an AI system, such as fittings or assemblies, including but not limited to unions, adapters, tees, crosses, manifolds, valves, etc. In addition, those skilled in the art will appreciate that the teachings herein can be implemented with a wide variety of process conditions, including various stationary phases and mobile phases, and at various operating pressures. For example, applicants have found that the embodiments herein can be operated above 12,000 psi, and even above 25,000 psi. Similarly, those of skill in the art will appreciate that they can apply the various embodiments of reinforcement inserts described herein, including those without an interior web, those with an interior web, and those in which the interior annular projection of the interior web is replaced with a biocompatible tube. As shown and described herein, the connectors are unitary, but those of ordinary skill in the art will appreciate that the reinforcement inserts and biocompatible connectors described in the drawings and above discussion can be formed from separate and distinct components. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

I claim:

1. A connector for use with an analytical instrument system, comprising:
    A) a reinforcement insert comprising an insert first end, an insert second end,
        a) a first portion proximal to the reinforcement insert first end,
            i) the first portion comprising a first end, a second end, an interior threaded section proximal the first end of the first portion, a first interior non-threaded section connected to the interior threaded section, a second interior non-threaded section connected to the first interior non-threaded section, and an exterior surface,
            ii) wherein the junction of the first interior non-threaded section and the second interior non-threaded section forms a first portion lip,
        b) a second portion proximal to the insert second end,
            i) the second portion comprising a first end, a second end, an interior threaded section proximal the first end of the second portion, a first interior non-threaded section connected to the first interior threaded section, a second interior non-threaded section connected to the first interior non-threaded section, and an exterior surface,
            ii) wherein the junction of the first interior non-threaded section and the second interior non-threaded section forms a second portion lip,
        c) and a middle portion between the first portion and the second portion,
            i) wherein the middle portion comprises an interior surface and an exterior surface,
            ii) and the middle portion defines a plurality of holes; and
    B) a biocompatible molding covering the second interior non-threaded section of the first portion, the second interior non-threaded section of the second portion, and the interior surface of the middle portion, a) wherein the biocompatible molding defines a passageway through the first portion, the second portion, and the middle portion.

2. The connector of claim 1, wherein the middle portion further comprises a biocompatible tube.

3. The connector of claim 1, wherein the exterior surface of the first portion or the exterior surface of the second portion has a hexagonal shape.

4. The connector of claim 1, wherein the biocompatible molding covers the exterior surface of the middle portion.

5. The connector of claim 1, wherein the biocompatible molding comprises PEEK.

6. The connector of claim 1, wherein the biocompatible molding comprises a first tapered section, a first non-tapered section connected to the first tapered section, a second tapered section, a second non-tapered section connected to the second tapered section, and an annular projection between the first non-tapered section and the second non-tapered section.

7. The connector of claim 1, further comprising a union.

8. The connector of claim 1, further comprising an adapter.

9. The connector of claim 1, further comprising a tee.

10. The connector of claim 1, further comprising a cross.

11. The connector of claim 1, further comprising a manifold.

12. The connector of claim 1, further comprising a plurality of core pins.

13. The connector of claim 1, wherein the middle portion comprises a groove.

14. The connector of claim 1, wherein the plurality of holes in the middle portion further comprise one or more slots.

15. The connector of claim 1, wherein the reinforcement insert is a unitary structure.

16. A connector for use with an analytical instrument system, comprising:
A) a reinforcement insert comprising an insert first end, an insert second end,
   a) a first portion proximal to the reinforcement insert first end,
      i) the first portion comprising a first end, a second end, an interior threaded section proximal the first end of the first portion, a first interior non-threaded section connected to the interior threaded section, a second interior non-threaded section connected to the first interior non-threaded section, and an exterior surface,
      ii) wherein the junction of the first interior non-threaded section and the second interior non-threaded section forms a first portion lip,
   b) a second portion proximal to the insert second end,
      i) the second portion comprising a first end, a second end, an interior threaded section proximal the first end of the second portion, a first interior non-threaded section connected to the first interior threaded section, a second interior non-threaded section connected to the first interior non-threaded section, and an exterior surface,
      ii) wherein the junction of the first interior non-threaded section and the second interior non-threaded section forms a second portion lip,
   c) and a middle portion between the first portion and the second portion, wherein the middle portion defines a plurality of holes, the middle portion comprising,
      i) an exterior surface,
      ii) a middle portion first interior non-tapered section adjacent to the first portion second interior non-threaded section,
      iii) a middle portion first interior tapered section connected to the middle portion first interior non-tapered section,
      iv) a middle portion second interior non-tapered section adjacent to the second portion second interior non-threaded section,
      v) a middle portion second interior tapered section connected to the middle portion second interior non-tapered section,
      vi) and a middle portion interior annular projection between the middle portion first interior tapered section and the middle portion second interior tapered section,
B) a biocompatible molding covering the second interior non-threaded section of the first portion, the second interior non-threaded section of the second portion, the middle portion first interior non-tapered section, the middle portion first interior tapered section, the middle portion second interior non-tapered section, and the middle portion second interior tapered section, wherein the biocompatible molding defines a passageway through the first portion, the second portion, and the middle portion.

17. The connector of claim 16, wherein the middle portion interior annular projection comprises a biocompatible tube.

18. The connector of claim 17, wherein the biocompatible tube comprises PEEK.

19. The connector of claim 17, wherein the biocompatible tube is coupled to the middle portion first interior tapered section and the middle portion second interior tapered section by an interference fit.

20. The connector of claim 17, wherein the biocompatible tube and biocompatible molding comprise different material.

21. The connector of claim 16, wherein the exterior surface of the first portion or the exterior surface of the second portion has a hexagonal shape.

22. The connector of claim 16, wherein the biocompatible molding covers the exterior surface of the middle portion.

23. The connector of claim 16, wherein the biocompatible molding comprises a first tapered section, a first non-tapered section, a second tapered section, and a second non-tapered section.

24. The connector of claim 16, further comprising a union.

25. The connector of claim 16, further comprising a tee.

26. The connector of claim 16, wherein the interior threaded section of the first portion has a different thread than interior threaded section of the second portion.

27. The connector of claim 16, further comprising a cross.

28. The connector of claim 16, further comprising a manifold.

29. The connector of claim 16, further comprising a plurality of core pins.

30. The connector of claim 16, wherein the biocompatible molding comprises PEEK.

31. The connector of claim 16, wherein the plurality of holes in the middle portion further comprise one or more slots.

32. The connector of claim 16, wherein the reinforcement insert comprises ceramic.

33. The connector of claim 16, wherein the reinforcement insert comprises steel.

34. The connector of claim 16, wherein the connector can withstand operating pressures above 12,000 psi.

35. An analytical instrument system, comprising:
A) a pump;
B) a detector;
C) a mobile phase;

D) a stationary phase;
E) at least one reinforcement insert comprising an insert first end, an insert second end,
  a) a first portion proximal to the reinforcement insert first end,
    i) the first portion comprising a first end, a second end, an interior threaded section proximal the first end of the first portion, a first interior non-threaded section connected to the interior threaded section, a second interior non-threaded section connected to the first interior non-threaded section, and an exterior surface,
    ii) wherein the junction of the first interior non-threaded section and the second interior non-threaded section forms a first portion lip,
  b) a second portion proximal to the insert second end,
    i) the second portion comprising a first end, a second end, an interior threaded section proximal the first end of the second portion, a first interior non-threaded section connected to the first interior threaded section, a second interior non-threaded section connected to the first interior non-threaded section, and an exterior surface,
    ii) wherein the junction of the first interior non-threaded section and the second interior non-threaded section forms a second portion lip,
  c) and a middle portion between the first portion and the second portion, wherein the middle portion defines a plurality of holes, the middle portion comprising,
    i) an exterior surface,
    ii) a middle portion first interior non-tapered section adjacent to the first portion second interior non-threaded section,
    iii) a middle portion first interior tapered section connected to the middle portion first interior non-tapered section,
    iv) a middle portion second interior non-tapered section adjacent to the second portion second interior non-threaded section,
    v) a middle portion second interior tapered section connected to the middle portion second interior non-tapered section,
    vi) and a middle portion interior annular projection between the middle portion first interior tapered section and the middle portion second interior tapered section,
F) a biocompatible molding covering the second interior non-threaded section of the first portion, the second interior non-threaded section of the second portion, the middle portion first interior non-tapered section, the middle portion first interior tapered section, the middle portion second interior non-tapered section, and the middle portion second interior tapered section, wherein the biocompatible molding defines a passageway through the first portion, the second portion, and the middle portion.

36. The analytical system of claim 35, wherein the analytical system can withstand operating pressures above 12,000 psi.

37. A method of manufacturing a biocompatible connector, the method comprising:
  A) providing a reinforcement insert, the reinforcement insert comprising:
    a) an insert first end, an insert second end,
      i) a first portion proximal to the reinforcement insert first end,
        a) the first portion comprising a first end, a second end, an interior threaded section proximal the first end of the first portion, a first interior non-threaded section connected to the interior threaded section, a second interior non-threaded section connected to the first interior non-threaded section, and an exterior surface,
      ii) wherein the junction of the first interior non-threaded section and the second interior non-threaded section forms a first portion lip,
    b) a second portion proximal to the insert second end,
      i) the second portion comprising a first end, a second end, an interior threaded section proximal the first end of the second portion, a first interior non-threaded section connected to the first interior threaded section, a second interior non-threaded section connected to the first interior non-threaded section, and an exterior surface,
      ii) wherein the junction of the first interior non-threaded section and the second interior non-threaded section forms a second portion lip,
    c) and a middle portion between the first portion and the second portion,
      i) wherein the middle portion comprises an interior surface and an exterior surface,
      ii) and the middle portion defines a plurality holes;
  B) coupling the reinforcement insert to at least one core pin;
  C) injecting biocompatible molded material into the reinforcement insert.

38. The method of claim 37, wherein the biocompatible molded material is injected into one or more holes of the middle portion of the reinforcement insert.

39. The method of claim 37, further comprising the step of removing at least one core pin from the reinforcement insert.

40. A biocompatible connector produced according to the method of claim 37.

* * * * *